United States Patent
Carlsson et al.

(10) Patent No.: US 12,292,355 B2
(45) Date of Patent: May 6, 2025

(54) OSTOMY LEAKAGE DETECTION SYSTEM

(71) Applicant: Hollister Incorporated, Libertyville, IL (US)

(72) Inventors: Jonas P. Carlsson, Chicago, IL (US); Ryan S. Park, Dallas, TX (US); Christina Augustyn, Chicago, IL (US); Kyle A. Matthews, Chapel Hill, NC (US); Scott E. Liddle, Raleigh, NC (US); Lauren M. Lattanzi, Raleigh, NC (US); Stephanie Musinsky, Raleigh, NC (US); Anthony B. Smith, Durham, NC (US); Robert A. Stevenson, Morrisville, NC (US)

(73) Assignee: HOLLISTER INCORPORATED, Libertyville, IL (US)

( * ) Notice: Subject to any disclaimer, the term of this patent is extended or adjusted under 35 U.S.C. 154(b) by 423 days.

(21) Appl. No.: 17/917,164

(22) PCT Filed: May 20, 2021

(86) PCT No.: PCT/US2021/033417
§ 371 (c)(1),
(2) Date: Oct. 5, 2022

(87) PCT Pub. No.: WO2021/242603
PCT Pub. Date: Dec. 2, 2021

(65) Prior Publication Data
US 2023/0160771 A1 May 25, 2023

Related U.S. Application Data

(60) Provisional application No. 63/139,034, filed on Oct. 5, 2022, provisional application No. 63/030,713, filed on Oct. 5, 2022.

(51) Int. Cl.
*A61F 5/445* (2006.01)
*A61F 5/44* (2006.01)
(Continued)

(52) U.S. Cl.
CPC ............... *G01M 3/16* (2013.01); *A61F 5/445* (2013.01)

(58) Field of Classification Search
CPC ........ A61F 5/4404; A61F 5/443; A61F 5/445; A61B 5/0002; A61B 5/4851; A61B 2560/02; G01M 3/16
See application file for complete search history.

(56) References Cited

U.S. PATENT DOCUMENTS 2,327,514 A * 8/1943 Fenwick ................. A61F 5/445
604/338
2,542,233 A * 2/1951 Carroll .................... A61F 5/445
604/337
(Continued)

FOREIGN PATENT DOCUMENTS

WO 2017/088153 A1 6/2017
WO 2019/094635 A1 5/2019
(Continued)

OTHER PUBLICATIONS

International Search Report issued by ISA/EPO in connection with PCT/US2021/033417 dated Sep. 14, 2021.
(Continued)

Primary Examiner — Guy K Townsend
(74) Attorney, Agent, or Firm — Klintworth & Rozenblat IP LLP

(57) ABSTRACT

An ostomy leakage detection system includes a sensing accessory, a wearable subsystem, a charging dock, and a mobile application. The sensing accessory includes a sensor region comprising a plurality of sensors for measuring
(Continued)

resistance of an ostomy appliance, a connector region for connecting to the wearable subsystem, and a tail region extending between the sensor region and the connector region.

20 Claims, 15 Drawing Sheets

(51) Int. Cl.
*A61F 5/443* (2006.01)
*G01M 3/16* (2006.01)

(56) References Cited

U.S. PATENT DOCUMENTS

| | | | | |
|---|---|---|---|---|
| 2,544,579 | A * | 3/1951 | Ardner | A61F 5/445 604/337 |
| 5,672,163 | A * | 9/1997 | Ferreira | A61F 5/441 604/333 |
| 6,135,986 | A * | 10/2000 | Leisner | A61F 5/441 604/324 |
| 6,171,289 | B1 * | 1/2001 | Millot | A61F 5/443 604/336 |
| 7,166,091 | B1 * | 1/2007 | Zeltner | A61F 5/445 604/338 |
| 7,326,190 | B2 * | 2/2008 | Botten | A61F 5/441 604/332 |
| 7,341,578 | B2 * | 3/2008 | Bulow | A61F 5/441 604/338 |
| 7,367,965 | B2 * | 5/2008 | Poulsen | A61F 5/441 604/324 |
| 7,559,922 | B2 * | 7/2009 | Botten | A61F 5/441 604/332 |
| 7,625,362 | B2 * | 12/2009 | Boehringer | A61M 1/74 604/304 |
| 7,670,289 | B1 * | 3/2010 | McCall | A61M 1/3655 210/651 |
| 7,981,098 | B2 * | 7/2011 | Boehringer | A61M 1/74 604/319 |
| 8,398,603 | B2 * | 3/2013 | Thirstrup | A61B 5/746 602/41 |
| 8,409,158 | B2 * | 4/2013 | Edvardsen | A61F 5/443 604/335 |
| 8,684,982 | B2 * | 4/2014 | Nguyen-DeMary | A61F 5/441 604/327 |
| 9,066,812 | B2 * | 6/2015 | Edvardsen | A61F 5/443 |
| 9,216,104 | B2 * | 12/2015 | Thirstrup | A61F 5/4404 |
| 9,308,332 | B2 * | 4/2016 | Heppe | A61M 1/30 |
| 10,016,298 | B2 * | 7/2018 | Thirstrup | A61F 13/42 |
| 10,500,084 | B2 * | 12/2019 | Hansen | A61F 5/445 |
| 10,646,370 | B2 * | 5/2020 | Keleny | A61F 5/441 |
| 10,799,385 | B2 * | 10/2020 | Hansen | G01M 3/40 |
| 10,849,781 | B2 * | 12/2020 | Hansen | G01N 27/041 |
| 10,987,243 | B2 * | 4/2021 | Thirstrup | A61B 5/746 |
| 11,096,818 | B2 * | 8/2021 | Thirstrup | A61F 13/02 |
| 11,291,577 | B2 * | 4/2022 | Seres | G16H 10/60 |
| 11,491,042 | B2 * | 11/2022 | Seres | G01F 23/261 |
| 11,534,323 | B2 * | 12/2022 | Hansen | A61F 2/64 |
| 11,547,595 | B2 * | 1/2023 | Hansen | A61F 5/44 |
| 11,547,596 | B2 * | 1/2023 | Hansen | A61F 5/44 |
| 11,559,423 | B2 * | 1/2023 | Speiermann | A61F 5/4404 |
| 11,559,426 | B2 * | 1/2023 | Sletten | A61F 5/44 |
| 2005/0070863 | A1 * | 3/2005 | Bulow | A61F 5/441 604/338 |
| 2005/0085779 | A1 * | 4/2005 | Poulsen | A61F 5/441 604/332 |
| 2005/0261645 | A1 * | 11/2005 | Conrad | A61F 5/445 604/332 |
| 2006/0025727 | A1 * | 2/2006 | Boehringer | A61M 1/966 604/313 |
| 2006/0271002 | A1 * | 11/2006 | Botten | A61F 5/441 604/339 |
| 2008/0091154 | A1 * | 4/2008 | Botten | A61F 5/441 96/155 |
| 2008/0275327 | A1 * | 11/2008 | Faarbaek | A61B 5/6833 600/382 |
| 2009/0012501 | A1 * | 1/2009 | Boehringer | A61M 1/966 604/543 |
| 2009/0247970 | A1 * | 10/2009 | Keleny | B01D 46/0036 156/247 |
| 2010/0010460 | A1 * | 1/2010 | Butler | A61F 5/441 604/333 |
| 2010/0030167 | A1 * | 2/2010 | Thirstrup | A61F 5/4404 340/657 |
| 2012/0143154 | A1 * | 6/2012 | Edvardsen | A61F 5/4404 604/336 |
| 2012/0143155 | A1 * | 6/2012 | Edvardsen | A61F 5/443 604/318 |
| 2012/0283678 | A1 * | 11/2012 | Nguyen-Demary | A61F 5/445 604/338 |
| 2013/0072886 | A1 * | 3/2013 | Schertiger | A61F 5/441 604/335 |
| 2013/0150769 | A1 * | 6/2013 | Heppe | A61M 1/3653 604/6.16 |
| 2013/0192604 | A1 * | 8/2013 | Persson | A61M 16/047 128/207.16 |
| 2013/0231620 | A1 * | 9/2013 | Thirstrup | A61F 5/445 604/344 |
| 2014/0276501 | A1 * | 9/2014 | Cisko | A61F 5/443 604/355 |
| 2014/0288381 | A1 * | 9/2014 | Faarbaek | A61B 5/0002 600/300 |
| 2015/0250639 | A1 * | 9/2015 | Thirstrup | A61F 13/00051 156/278 |
| 2016/0158056 | A1 * | 6/2016 | Davis | A61F 5/443 29/872 |
| 2016/0166438 | A1 * | 6/2016 | Rovaniemi | A61B 5/00 493/320 |
| 2016/0235581 | A1 * | 8/2016 | Keleny | A61F 5/441 |
| 2017/0140103 | A1 * | 5/2017 | Angelides | A61F 5/4404 |
| 2017/0340474 | A1 * | 11/2017 | Thirstrup | A61B 5/746 |
| 2018/0344533 | A1 * | 12/2018 | Rovaniemi | A61F 13/0209 |
| 2019/0133810 | A1 * | 5/2019 | Seres | A61B 5/445 |
| 2019/0133811 | A1 * | 5/2019 | Seres | A61F 5/4404 |
| 2019/0133812 | A1 * | 5/2019 | Seres | A61F 5/443 |
| 2019/0142623 | A1 | 5/2019 | Norman et al. | |
| 2019/0175386 | A1 * | 6/2019 | Monty | A61F 13/0266 |
| 2019/0192332 | A1 * | 6/2019 | Hansen | A61F 5/4404 |
| 2019/0192333 | A1 * | 6/2019 | Hansen | A61B 5/6833 |
| 2019/0192334 | A1 * | 6/2019 | Hansen | A61F 5/445 |
| 2019/0240059 | A1 * | 8/2019 | Seres | A61F 5/445 |
| 2019/0247050 | A1 * | 8/2019 | Goldsmith | A61F 2/82 |
| 2019/0374163 | A1 * | 12/2019 | Faarbaek | A61B 5/411 |
| 2019/0374372 | A1 * | 12/2019 | Seres | A61B 5/6802 |
| 2020/0000624 | A1 * | 1/2020 | Gibbons | A61B 5/444 |
| 2020/0188161 | A1 * | 6/2020 | Seres | G01K 13/00 |
| 2020/0246174 | A1 * | 8/2020 | Hansen | A61F 5/443 |
| 2020/0246175 | A1 * | 8/2020 | Hansen | G01M 3/16 |
| 2020/0246176 | A1 * | 8/2020 | Hansen | A61F 5/445 |
| 2020/0246177 | A1 * | 8/2020 | Hansen | A61F 5/445 |
| 2020/0306074 | A1 * | 10/2020 | Speiermann | A61F 5/4404 |
| 2020/0330258 | A1 * | 10/2020 | Hansen | A61F 13/511 |
| 2020/0330260 | A1 * | 10/2020 | Hansen | G16H 50/30 |
| 2020/0337880 | A1 * | 10/2020 | Hansen | A61F 5/443 |
| 2020/0337881 | A1 * | 10/2020 | Hansen | A61F 5/4404 |
| 2020/0337883 | A1 * | 10/2020 | Hansen | A61F 5/4404 |
| 2020/0375784 | A1 * | 12/2020 | Hansen | A61F 5/443 |
| 2020/0375785 | A1 * | 12/2020 | Hansen | G16H 30/40 |
| 2020/0375786 | A1 * | 12/2020 | Hansen | A61F 5/443 |
| 2020/0383637 | A1 * | 12/2020 | Hansen | A61B 5/7405 |
| 2020/0383818 | A1 * | 12/2020 | Hansen | A61F 5/443 |
| 2020/0383819 | A1 * | 12/2020 | Sletten | A61F 5/44 |
| 2020/0383820 | A1 * | 12/2020 | Hansen | G16H 40/40 |
| 2020/0383821 | A1 * | 12/2020 | Hansen | A61F 5/443 |
| 2020/0390587 | A1 * | 12/2020 | Svanegaard | G16H 40/40 |
| 2020/0390588 | A1 * | 12/2020 | Hansen | A61F 5/4404 |
| 2020/0390589 | A1 * | 12/2020 | Hansen | A61F 5/443 |
| 2020/0395120 | A1 * | 12/2020 | Svanegaard | G06F 3/0482 |
| 2020/0405228 | A1 * | 12/2020 | Svanegaard | A61F 5/4404 |
| 2020/0405229 | A1 * | 12/2020 | Svanegaard | A61B 5/4851 |

(56) References Cited

U.S. PATENT DOCUMENTS

| | | | |
|---|---|---|---|
| 2020/0405230 A1* | 12/2020 | Svanegaard | A61B 5/6813 |
| 2021/0000414 A1* | 1/2021 | Svanegaard | A61F 5/4404 |
| 2021/0000633 A1* | 1/2021 | Hansen | G01K 13/00 |
| 2021/0000634 A1* | 1/2021 | Svanegaard | A61B 5/0004 |
| 2021/0000635 A1* | 1/2021 | Hansen | A61F 5/443 |
| 2021/0007663 A1* | 1/2021 | Svanegaard | G16H 40/40 |
| 2021/0007881 A1* | 1/2021 | Svanegaard | A61B 5/002 |
| 2021/0015654 A1* | 1/2021 | Hansen | A61F 5/445 |
| 2021/0038424 A1* | 2/2021 | Svanegaard | A61B 5/6843 |
| 2021/0059603 A1* | 3/2021 | Svanegaard | H04M 1/72409 |
| 2021/0085511 A1* | 3/2021 | Hansen | A61F 5/445 |
| 2021/0085512 A1* | 3/2021 | Hansen | A61B 5/4851 |
| 2021/0100533 A1* | 4/2021 | Seres | A61B 5/42 |
| 2021/0177642 A1* | 6/2021 | Andersen | G16H 40/67 |
| 2021/0212855 A1* | 7/2021 | Hansen | A61F 5/443 |
| 2021/0275341 A1* | 9/2021 | Hansen | A61F 5/443 |
| 2021/0338471 A1* | 11/2021 | Nolan | A61F 5/448 |
| 2021/0353448 A1 | 11/2021 | George et al. | |
| 2021/0361464 A1* | 11/2021 | Larsen | A61F 5/443 |
| 2021/0361465 A1* | 11/2021 | Hansen | A61B 5/4851 |
| 2021/0361467 A1* | 11/2021 | Hansen | A61F 5/4404 |
| 2021/0369197 A1* | 12/2021 | Hansen | A61F 5/443 |
| 2021/0369488 A1* | 12/2021 | Hansen | A61F 5/4404 |
| 2021/0369489 A1* | 12/2021 | Hansen | A61F 5/4404 |
| 2021/0369490 A1* | 12/2021 | Hansen | A61F 5/4404 |
| 2021/0369491 A1 | 12/2021 | Holden | |
| 2022/0117771 A1 | 4/2022 | Fearn et al. | |
| 2022/0257405 A1* | 8/2022 | Moeller | A61F 5/445 |
| 2022/0265457 A1* | 8/2022 | Emborg | A61F 5/4404 |
| 2022/0313473 A1* | 10/2022 | Schertiger | A61F 5/445 |
| 2022/0378602 A1* | 12/2022 | Hansen | A61F 5/4404 |
| 2023/0031979 A1* | 2/2023 | Windeballe | A61F 5/443 |

FOREIGN PATENT DOCUMENTS

| | | | |
|---|---|---|---|
| WO | 2019/120424 A1 | 6/2019 | |
| WO | 2019/120425 A1 | 6/2019 | |
| WO | 2019/120426 A1 | 6/2019 | |
| WO | 2019/120427 A1 | 6/2019 | |
| WO | 2019/120428 A1 | 6/2019 | |
| WO | 2019/120429 A1 | 6/2019 | |
| WO | 2019/120430 A1 | 6/2019 | |
| WO | 2019/120432 A1 | 6/2019 | |
| WO | 2019/120433 A1 | 6/2019 | |
| WO | 2019/120434 A1 | 6/2019 | |
| WO | 2019/120435 A1 | 6/2019 | |
| WO | 2019/120436 A1 | 6/2019 | |
| WO | 2019/120437 A1 | 6/2019 | |
| WO | 2019/120440 A1 | 6/2019 | |
| WO | 2019/120441 A1 | 6/2019 | |
| WO | 2019/120442 A1 | 6/2019 | |
| WO | 2019/120443 A1 | 6/2019 | |
| WO | 2019/120444 A1 | 6/2019 | |
| WO | 2019/120445 A1 | 6/2019 | |
| WO | 2019/120448 A1 | 6/2019 | |
| WO | 2019/120449 A1 | 6/2019 | |
| WO | 2019/120450 A1 | 6/2019 | |
| WO | 2019/120451 A1 | 6/2019 | |
| WO | 2019/120452 A1 | 6/2019 | |
| WO | 2019/120453 A1 | 6/2019 | |
| WO | 2019/120458 A1 | 6/2019 | |
| WO | WO-2019120446 A1 * | 6/2019 | A61B 5/4266 |
| WO | 2019/149330 A1 | 8/2019 | |
| WO | 2019/161859 A1 | 8/2019 | |
| WO | 2019/161860 A1 | 8/2019 | |
| WO | 2019/161861 A1 | 8/2019 | |
| WO | 2019/161862 A1 | 8/2019 | |
| WO | 2019/161863 A1 | 8/2019 | |
| WO | 2019/174687 A1 | 9/2019 | |
| WO | 2019/174692 A1 | 9/2019 | |
| WO | 2019/174693 A1 | 9/2019 | |
| WO | 2019/174694 A1 | 9/2019 | |
| WO | 2019/174695 A1 | 9/2019 | |
| WO | 2019/174696 A1 | 9/2019 | |
| WO | 2019/174697 A1 | 9/2019 | |
| WO | 2019/174698 A1 | 9/2019 | |
| WO | 2019/174699 A1 | 9/2019 | |
| WO | 2019/238180 A1 | 12/2019 | |
| WO | 2019/238181 A1 | 12/2019 | |
| WO | 2019/238182 A1 | 12/2019 | |
| WO | 2019/238183 A1 | 12/2019 | |
| WO | 2020/035121 A1 | 2/2020 | |
| WO | 2020/123771 A2 | 6/2020 | |
| WO | 2020/156624 A1 | 8/2020 | |
| WO | 2020/156625 A1 | 8/2020 | |
| WO | 2020/156626 A1 | 8/2020 | |
| WO | 2020/169162 A1 | 8/2020 | |
| WO | 2020/173534 A1 | 9/2020 | |
| WO | 2020/216426 A1 | 10/2020 | |
| WO | 2020/216427 A1 | 10/2020 | |
| WO | 2020/216429 A1 | 10/2020 | |
| WO | 2020/259775 A1 | 12/2020 | |
| WO | 2021/063463 | 4/2021 | |
| WO | 2021/063466 A1 | 4/2021 | |
| WO | 2021/165703 A1 | 8/2021 | |
| WO | 2021/165705 A1 | 8/2021 | |
| WO | 2021/185425 A1 | 9/2021 | |
| WO | 2021/209104 A1 | 10/2021 | |
| WO | 2021/242603 A1 | 12/2021 | |
| WO | 2022/063379 A1 | 3/2022 | |
| WO | 2022/078561 A1 | 4/2022 | |
| WO | 2022/207049 A1 | 10/2022 | |

OTHER PUBLICATIONS

Written Opinion issued by ISA/EPO in connection with PCT/US2021/033417 dated Sep. 14, 2021.

International Preliminary Report on Patentability issued by WIPO in connection with PCT/US2021/033417 dated Dec. 8, 2022.

* cited by examiner

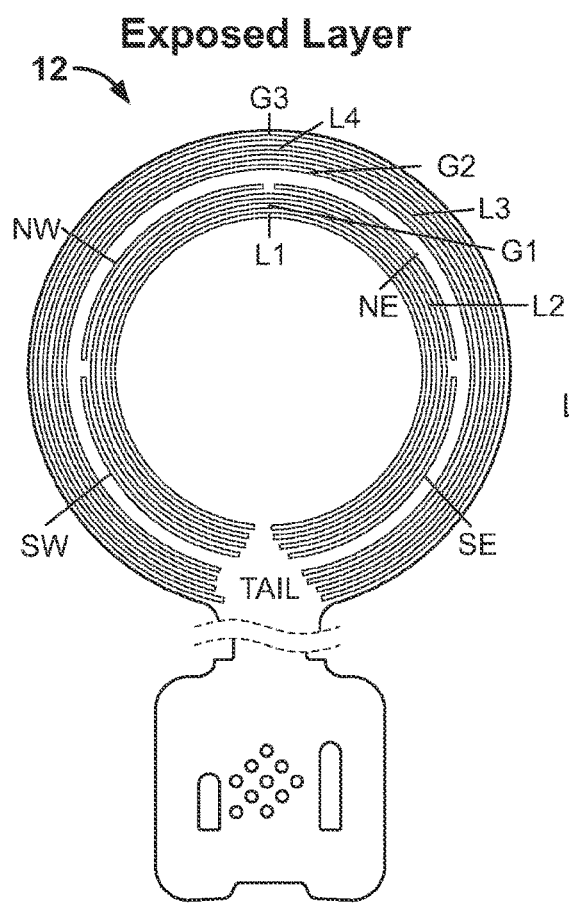
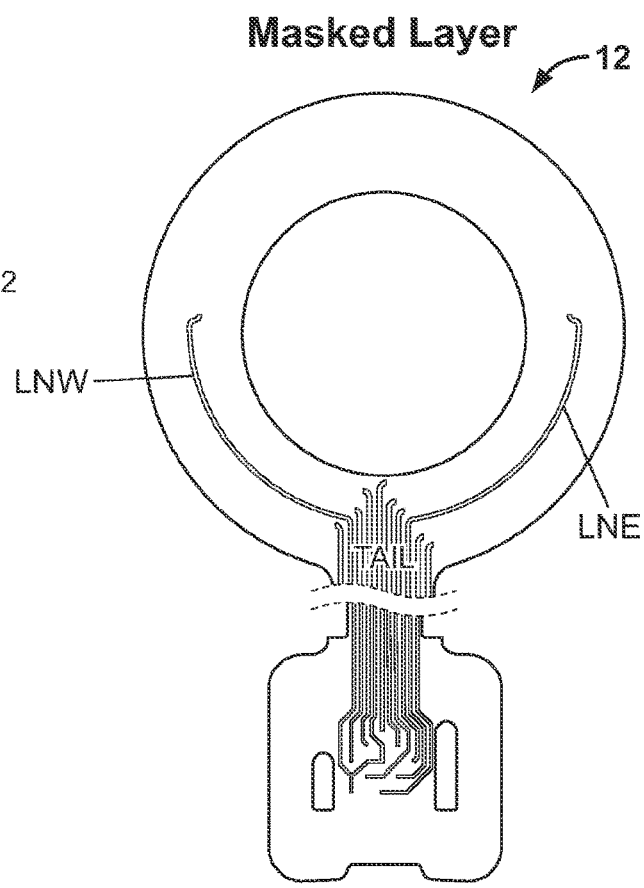
FIG. 5A
FIG. 5B

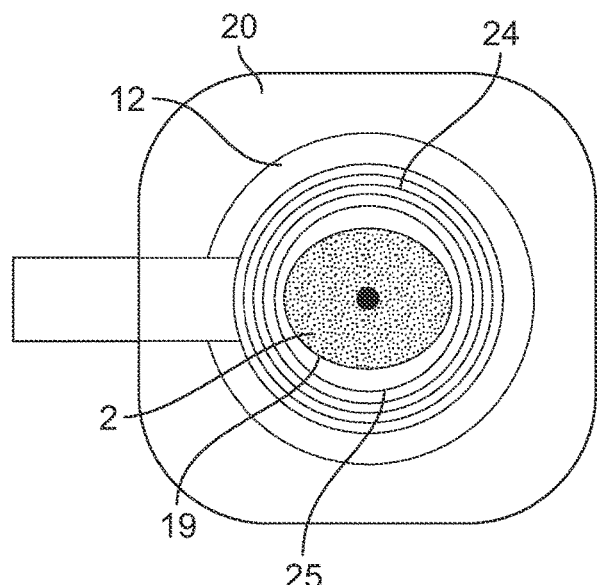
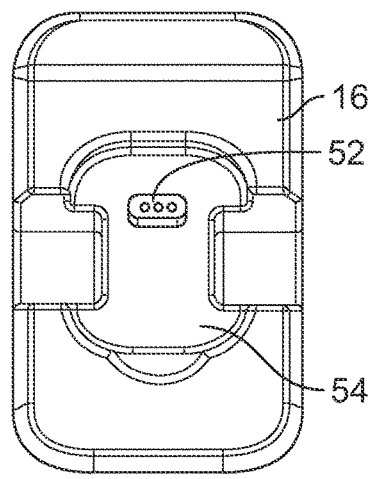
FIG. 22
FIG. 23A
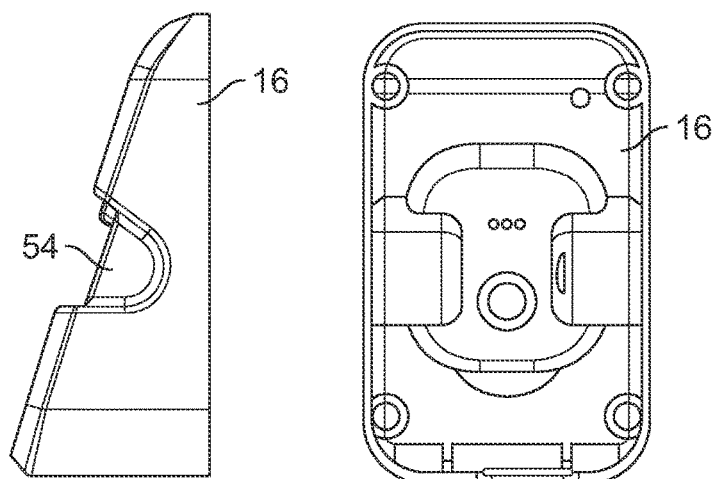
FIG. 23B
FIG. 23C
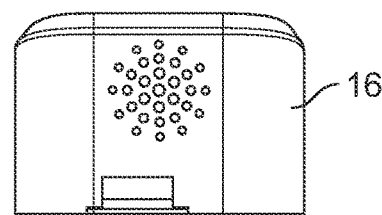
FIG. 23D

OSTOMY LEAKAGE DETECTION SYSTEM

This is a National Stage Application of International Patent Application No. PCT/US2021/033417 filed May 20, 2021, which claims the benefit of and priority to U.S. Provisional Application No. 63/030,713 filed May 27, 2020 and U.S. Provisional Application No. 63/139,034 filed Jan. 19, 2021, the entireties of which are incorporated fully herein by references.

BACKGROUND

The following description relates generally to a leakage detection system for medical devices, and more particularly to leakage detection system for ostomy appliances.

An ostomy pouch system typically includes a pouch formed from opposing walls defining an internal collection area, an inlet opening for receiving a stoma, and an ostomy appliance for attaching the pouch to a user. The ostomy appliance may include, for example, an ostomy barrier of a one-piece pouch system, which is attached to a body-side pouch wall proximate an inlet opening, a baseplate for a two-piece pouch system configured to releasably engage a pouch, and a barrier ring. The ostomy appliance may include a skin barrier material for adhering to and sealing against user's peristomal skin surrounding the stoma.

The ostomy appliance may be susceptible to ostomy effluent leakage, and the seal formed between the skin barrier material and the user may weaken. Often times, the user may be unaware of or cannot easily assess an extent of weakening in the seal. Thus, the user may not become aware of a weakened seal, and consequently, the ostomy effluent may leak through to an exterior of the ostomy appliance.

Accordingly, it is desirable to provide a leakage detection system for ostomy appliances.

BRIEF SUMMARY

In one aspect, a sensing accessory for detecting leakage in a medical device is provided. The sensing accessory may include a sensor region, a connector region, and an elongated tail region extending therebetween. The sensor region may comprise a center opening and a plurality of sensors arranged around the center opening. The plurality of sensors may include at least two substantially elliptical conductive traces substantially surrounding the center opening and at least two arc-shaped conductive traces. The at least two substantially elliptical conductive traces may include a first trace and a second trace, and the at least two arc-shaped conductive traces may include a first arc trace and a second arc trace. Each of the two substantially elliptical conductive traces may be arranged at a different radial distance from the center opening, and each of the at least two arc-shaped conductive traces may be arranged in a different sector in the sensor region. The connector region may include a plurality of connection points provided at terminal ends of the plurality of sensors for electrical connection to an external device.

In an embodiment, the first trace may be arranged at a first radial distance from the center opening, the second trace may be arranged at a second radial distance from the center opening, the first arc trace may be arranged at a third radial distance from the center opening, and the second arc trace may be arranged at a fourth radial distance from the center opening, wherein the third and fourth radial distances are greater than the second radial distance and the second radial distance is greater than the first radial distance. In such an embodiment, the first trace, the second trace, and the first and second arc traces may be arranged in three substantially concentric layers substantially surrounding the center opening. The sensing accessory may be configured to measure a resistance of the medical device between the first trace and the second trace and between the second trace and each of the at least two arc-shaped conductive traces.

In an embodiment, the first trace may be a first level trace and the second trace may be a first ground trace, and the at least two substantially elliptical conductive traces may further include a second level trace, a fourth level trace, a fifth level trace, a second ground trace, and a third ground trace, and the at least two arc-shaped conductive traces may further include a third arc trace and a fourth arc trace. The first level trace may be arranged at a first radial distance from the center opening, the first ground trace may be arranged at a second radial distance from the center opening, a second level trace may be arranged at a third radial distance from the center opening, the second ground trace may be arranged at a fifth radial distance from the center opening, the fourth level trace may be arranged at a sixth radial distance from the center opening, the fifth level trace may be arranged at a seventh radial distance from the center opening, the third ground trace may be arranged at an eighth radial distance from the center opening, and the first, second, third, and fourth arc traces may be arranged at a fourth radial distance from the center opening, wherein a radial distance may increase from the first radial distance to the eighth radial distance, wherein first radial distance<second radial distance<third radial distance<fourth radial distance<fifth radial distance<sixth radial distance<seventh radial distance<eighth radial distance. In such an embodiment, the level traces, the ground traces, and the arc traces may be arranged in eight substantially concentric layers substantially surrounding the center opening. The sensing accessory may be configured to measure a resistance of the medical device between the first level trace and the first ground trace, between the first ground trace and the second level trace, between each of the first, second, third, and fourth arc traces and the second ground trace, between the second ground trace and the fourth level trace, and between the fifth level trace and the third ground trace.

Each of the first, second, third, and fourth arc traces may be arranged in a different quadrant in the sensor region. For example, the first, second, third, and fourth arc traces may be arranged in intercardinal directions of the sensor region with the tail region being arranged at south. In such an embodiment, the first arc trace may extend along a southeast (SE) quadrant of the sensor region. The second arc trace may be formed from an exposed portion of a curved conductive trace extending along an east half of the sensor region, wherein a lower portion of the curved conductive trace may be covered with a masking layer to provide the second arc trace extending along a northeast (NE) quadrant of the sensor region. The third arc trace may be formed from an exposed portion of a curved conductive trace extending along an west half of the sensor region, wherein a lower portion of the curved conductive trace may be covered with a masking layer to provide the third arc trace extending along a northwest (NW) quadrant of the sensor region. The fourth arc trace may extend along a southwest (SW) quadrant of the sensor region.

In such an embodiment, the sensing accessory may be configured to measure a resistance of the medical device between the first level trace and the first ground trace for determination of a level 1 leakage, a resistance between the first ground trace and the second level trace for determination of a level 2 leakage, a resistance between the first arc trace and the second ground trace for determination of a level 3 leakage in the SE quadrant, a resistance between the second arc trace and the second ground trace for determination of a level 3 leakage in the NE quadrant, a resistance between the third arc trace and the second ground trace for determination of a level 3 leakage in the NW quadrant, a resistance between the fourth arc trace and the second ground trace for determination of a level 3 leakage in the SW quadrant, a resistance between the second ground trace and fourth level trace for determination of a level 4 leakage, and a resistance between the fifth level trace and the third ground trace for determination of a level 5 leakage. The severity of a leakage may increase from level 1 leakage to level 5 leakage, wherein level 1 leakage<level 2 leakage<level 3 leakage<level 4 leakage<level 5 leakage, wherein the level 5 leakage may be a critical leakage.

In another embodiment, the at least two substantially elliptical conductive traces may include first, second, third, and fourth traces, and the at least two arc-shaped conductive traces may include first, second, third and fourth arc traces. The first trace may be arranged at a first radial distance from the center opening, the second trace may be arranged at a second radial distance from the center opening, a third trace may be arranged at a fourth radial distance from the center opening, the fourth trace may be arranged at a fifth radial distance from the center opening, and the first, second, third, and fourth arc traces are arranged at a third radial distance from the center opening, wherein a radial distance may increase from the first radial distance to the fifth radial distance, wherein first radial distance<second radial distance<third radial distance<fourth radial distance<fifth radial distance. In such an embodiment, the first, second, third, and fourth traces, and the first, second, third, and fourth arc traces may be arranged in five substantially concentric layers substantially surrounding the center opening, wherein the first arc trace extends along a SE quadrant, the second arc trace extends along a NE quadrant, the third arc trace extends along a NW quadrant, and the fourth arc trace extends along a SW quadrant of the sensor region.

In such an embodiment, the sensing accessory may be configured to measure a resistance of the medical device between the first trace and the second trace for determination of a level 1 leakage, a resistance between the second trace and the first arc trace for determination of a level 2 leakage in the SE quadrant, a resistance between the second trace and the second arc trace for determination of a level 2 leakage in the NE quadrant, a resistance between the second trace and the third arc trace for determination of a level 2 leakage in the NW quadrant, a resistance between the second trace and the fourth arc trace for determination of a level 2 leakage in the SW quadrant, a resistance between the first arc trace and the third trace for determination of a level 3 leakage in the SE quadrant, a resistance between the second arc trace and the third trace for determination of a level 3 leakage in the NE quadrant, a resistance between the third arc trace and the third trace for determination of a level 3 leakage in the NW quadrant, a resistance between the fourth arc trace and the third trace for determination of a level 3 leakage in the SW quadrant, and a resistance between the third trace and fourth trace to determine a level 4 leakage. The severity of a leakage may increase from level 1 to level 4, wherein level 1 leakage<level 2 leakage<level 3 leakage<level 4 leakage, wherein the level 4 leakage may be a critical leakage.

In any of the foregoing embodiments, the medical device may be an ostomy appliance including an adhesive layer configured for attachment to a peristomal skin of a user, wherein the plurality of sensors may be arranged adjacent the adhesive layer to measure a resistance of the adhesive layer.

In an embodiment, the sensor region may have a ring-like shape, and the center opening may be configured to receive a stoma. Each of the at least two substantially elliptical conductive traces and the at least two arc-shaped conductive traces may extend from the sensor region through the tail region to the connector region and terminate at the plurality of connection points.

The sensing accessory may include a sensor layer having a body-side and a distal side, an adhesive layer arranged on the body-side of the sensor layer, and a backing layer arranged on the distal side of the sensor layer. The sensor layer may include a substrate, wherein the plurality of sensors may be provided on a body-side of the substrate and in contact with the adhesive layer. The sensing accessory may be configured to measure a resistance of the adhesive layer using the plurality of sensors.

In an embodiment, the backing layer may be formed from an adhesive. In such an embodiment, the sensing accessory may include a body-side release liner covering the adhesive layer and a distal side release liner covering the backing layer. Each of the release liners may include a tab configured to facilitate removal of the release liners, wherein the tabs may be arranged offset from each other. In some embodiments, the release liners may include indicator labels to guide assembling of the sensing accessory with an ostomy appliance and attachment of the assembled sensing accessory and ostomy appliance to a user.

In an embodiment, exposed portions of the tail region of the sensor layer may be covered with a tail cover. The tail cover may also cover a portion of the connector region and include a wing-like extensions in the connector region, wherein an adhesive is provided on the wing-like extensions for attachment to an ostomy pouch or a user.

In an embodiment, the sensing accessory may be configured to attach to an ostomy barrier. In such an embodiment, the backing layer may be attached to the ostomy barrier, and the adhesive layer may be attached to a peristomal skin of a user. The adhesive layer may be formed from a hydrocolloid adhesive configured to exhibit a resistance drop from greater than 2 M$\Omega$ to about 1 k$\Omega$ when exposed to an ostomy effluent.

In an embodiment, the sensing accessory may be configured to stretch to conform to a convex ostomy barrier, wherein the substrate and the plurality of sensors may be formed from stretchable materials.

In another aspect, a leakage detection system for an ostomy appliance is provided. The leakage detection system may include the sensing accessory according to any of the foregoing embodiments and a wearable subsystem configured to communicate with the sensing accessory and receive signals from the sensing accessory to detect an ostomy effluent leakage.

In an embodiment, the wearable subsystem may include a hinged case comprising a bottom housing, a top housing, and a hinge connecting the bottom housing and the top housing. The hinged case may be configured to be closed after the wearable subsystem is connected to the connector region to secure the wearable subsystem to the sensing accessory.

In some embodiments, the sensing accessory may include a first alignment member and the wearable subsystem may include a second alignment member, which may be configured to engage with each other to facilitate correct alignment and connection between the sensing accessory and the wearable subsystem. The first alignment member may include at least one opening in the connector region of the sensing accessory, and the second alignment member may include at least one raised member, wherein the at least one raised member may be configured to be received in the at least one opening.

In an embodiment, the second alignment member may include a center raised key member and a peripheral raised member. The center raised key member may be provided generally in the center of the bottom housing and the peripheral raised member may be arranged proximate the hinge. The first alignment member may include a center key opening configured to receive the center raised key member and a peripheral opening configured to receive the peripheral raised member. The wearable subsystem may further include a plurality of conductive members configured to contact the plurality of connection points to electrically connect the wearable subsystem to the sensing accessory. The plurality of conductive members may be arranged proximate and surrounding the center raised key member.

In another embodiment, the second alignment member may include first and second raised members. The first alignment member may include a first opening configured to receive the first raised member and a second opening configured to receive the second raised member. In such an embodiment, the wearable subsystem may also include a plurality of conductive members arranged between the first and second raised member for electrically connecting the wearable subsystem to the sensing accessory.

In an embodiment, the leakage detection system may include a charging dock configured to connect to the wearable subsystem to charge a rechargeable battery of the wearable subsystem. The charging dock may also be configured to wirelessly communicate with the wearable subsystem to receive leakage signals and send an alert to a user.

In an embodiment, the plurality of conductive members may comprise a plurality of raised conductive pads.

In any of the foregoing embodiments, the tail region may be flexible to allow the wearable subsystem to be attached to a user or to the ostomy appliance at various locations when the wearable subsystem is attached to the sensor accessory.

The wearable subsystem may be configured to analyze signals received from the sensing accessory, communicate with external devices, and alert a user to notify a leakage event and/or a status of the ostomy appliance, for example, via sound, vibration, and/or light. In an embodiment, the wearable subsystem may be configured to poll resistance measurements from the plurality of sensors to collect resistance data and process the resistance data through an algorithm to determine an ostomy effluent leakage event, and alert a user according the severity of the leakage event. The wearable subsystem may also be configured to detect and communicate a connectivity status between the wearable subsystem and the sensing accessory and a faulty sensor to a user or to an external device.

In some embodiments, the wearable subsystem may include a rechargeable battery. In such embodiments, the leakage detection system may further include a charging dock for charging the rechargeable battery of the wearable subsystem. The charging dock may also be configured to wirelessly communicate with the wearable subsystem to receive leakage signals and send an alert to a user.

In an embodiment, the charging dock may comprise a housing configured to receive the wearable subsystem and charging pins. The wearable subsystem may include conductive pads configured to electrically connect to the charging pins. The charging dock may also include a device for generating a sound and/or light to alert a user and a wireless communication module for communicating with the wearable subsystem and/or a mobile application.

In an embodiment, the leakage detection system may also include a mobile application configured to wirelessly communicate with the wearable subsystem and/or the charging dock. The mobile application may be provided as an application for a mobile phone. In such an embodiment, the wearable subsystem may be configured to transmit data to the mobile application. The transmitted data may include raw resistance measurements as received from the sensing accessory and/or processed data generated by processing the resistance measurements at the wearable subsystem. The processed data may include a leakage event information and/or a summary of the resistance measurements.

The mobile application may be configured to provide means for a user to interact with the leakage detection system to set user's preferences for alerts and to review information about the ostomy appliance. The information may include leakage patterns, historical data of user's ostomy appliance usage, and/or ostomy appliance usage trends. The mobile application may also be configured to connect a user to ostomy training materials, experts at ostomy appliance suppliers, and/or ostomy clinicians. Further, the mobile application may be configured to check a connectivity between the mobile application and the wearable subsystem and/or a connectivity between the mobile application and the charging dock and alert a user.

In an embodiment, the mobile application may be configured to receive a leakage event information from the wearable subsystem and alert a user through alert functions of a mobile phone. Further, the mobile application may be configured to transmit data to a cloud server for storage and analysis to provide a prediction of a leakage event based on user's historical data, comparison data against leakage patterns of other users, product recommendations based on user's leakage patterns, and/or a prompt for re-ordering ostomy products. The mobile application may also be configured to manage a storage of photographs of user's stoma and/or peristomal skin for tracking with user's leakage patterns.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein:

FIGS. 5A-5C are schematic illustrations of leakage sensors comprising a plurality of conductive traces, wherein some portions of the conductive traces are masked, according an embodiment;

FIG. 22 is a schematic illustration of a sensing accessory attached to an ostomy skin barrier and fitted around a stoma according to an embodiment;

FIGS. 23A-24D are illustrations of a charging dock according to an embodiment;

FIG. 24 is a block diagram for a method of detecting an ostomy effluent according to an embodiment.

DETAILED DESCRIPTION

Figure 1:
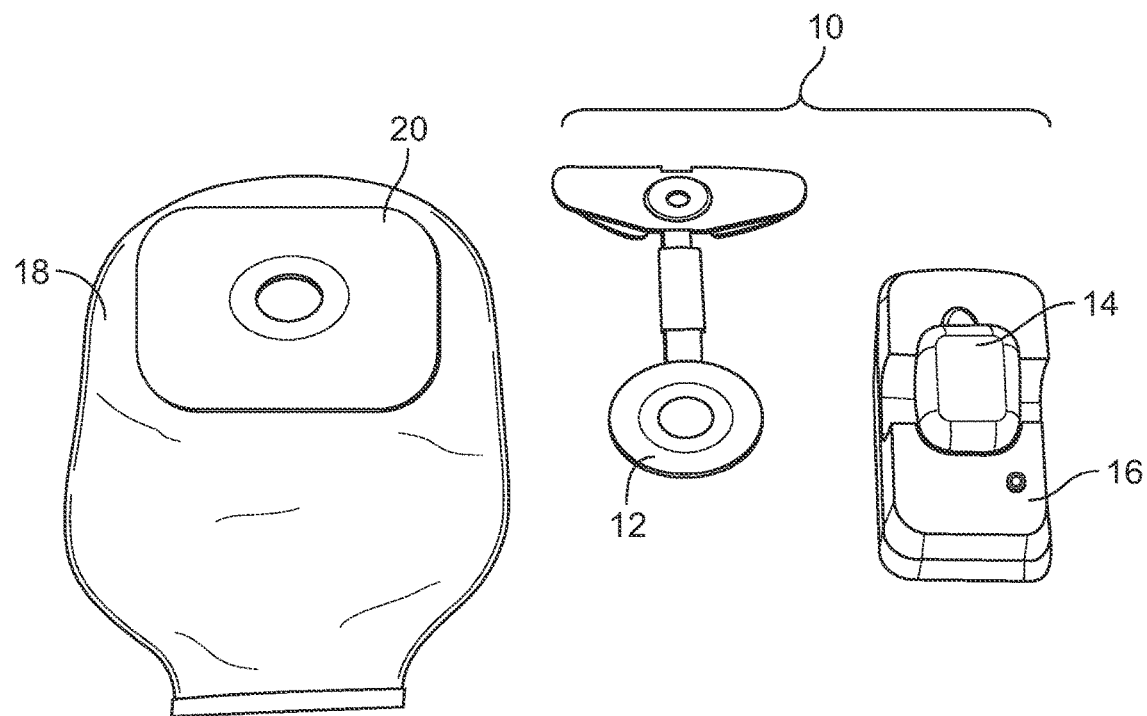
FIG. 1 is a perspective illustration of an ostomy pouch appliance and a leakage detection system according to an embodiment.

While the present disclosure is susceptible of embodiment in various forms, there is shown in the drawings and will hereinafter be described presently preferred embodiments with the understanding that the present disclosure is to be considered an exemplification and is not intended to limit the disclosure to the specific embodiments illustrated. The words "a" or "an" are to be taken to include both the singular and the plural. Conversely, any reference to plural items shall, where appropriate, include the singular.

An ostomy leakage detection system may be configured to detect ostomy effluent leakage under a skin barrier and alert a user. The ostomy leakage detection system can provide multiple benefits to the user. For example, the system may allow the user to intervene and change a skin barrier and/or ostomy pouch system before a leak progresses to cause embarrassment and inconvenience to the user. Further, the ostomy leakage detection system can assist in maintaining user's skin health by alerting a leakage in its early stage to prevent a prolonged skin exposure to ostomy effluent, which can lead to skin health complications. The ostomy leakage detection system can also support user's emotional well-being by reducing anxiety associated with a risk of leakage.

In an embodiment, the ostomy leakage detection system may comprise four subsystems—a sensing accessory, a wearable subsystem, a mobile application, and a charging dock. The sensing accessory may be provided as an accessory for an ostomy pouch system. The sensing accessory may include sensors for detecting the presence of ostomy effluent. The sensing accessory may be configured to communicates leakage detection signals to the wearable subsystem. The wearable subsystem may be configured to perform at least some processing of the leakage detection signals and alert a user of a leakage event. The wearable subsystem may be configured to communicate wirelessly with the mobile application. The mobile application may be a digital subsystem housed on a mobile device. The mobile application may be configured to process leak detection data and provide an alert or other information about an ostomy appliance to a user. The charging dock may be configured to recharge and communicate with the wearable subsystem and send out an alert, for example, when the system is in use at night.

FIG. 1 shows an ostomy leakage detection system 10 according to an embodiment. The ostomy leakage detection system 10 may generally comprise a sensing accessory 12, a wearable subsystem 14, a charging dock 16, and a mobile application (not shown). The sensing accessory 12 may be configured as an ostomy accessory that can be attached to an ostomy skin barrier, for example, an ostomy barrier of a one-piece pouch system or a faceplate for a two-piece pouch system. A one-piece ostomy pouch system 18 comprising an ostomy barrier 20 according to an embodiment is shown in FIG. 1.

Sensing Accessory

The sensing accessory may be configured to detect an ostomy effluent leakage by providing sensors at a site of leakage under an ostomy barrier. The sensing accessory may comprise a plurality of sensors configured to detect the presence of fluid. The plurality of sensors may include conductivity sensors, thermistors, or other sensors. In an embodiment, the sensing accessory may comprise a plurality of conductivity sensors formed from conductive traces arranged in close proximity. The conductive traces are also referred to herein as electrodes. When fluid bridges the conductive traces or saturates an adjacent hydrocolloid adhesive, a change in conductivity may be measured, which may be used to determine an ostomy effluent leakage. The sensors may be disposed on a circuit substrate. The circuit substrate may be configured to provide a suitable mechanical support to preserve the conductivity of the traces.

The conductive traces may be formed by printing a circuit substrate using a conductive ink via a conventional printing process, for example, screen printing. The conductive ink may comprise carbon black, graphite, silver (Ag), or a silver and silver chloride blend (Ag/AgCl). Each of the plurality of conductive traces may have a width and arranged spaced apart from each other. The parameters of the conductive traces may be configured to provide a particular resistance of a sensor circuit.

Figure 2:
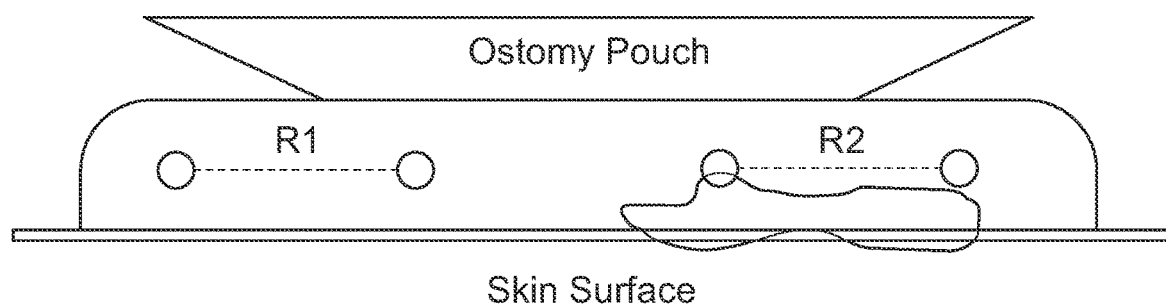
FIG. 2 is a schematic illustration of an ostomy pouch appliance including leakage detection sensors according to an embodiment.

In an embodiment, the sensing accessory may be configured to detect a leakage based on a change in resistance across a pair of conductive traces making up a sensor. FIG. 2 is a schematic cross-sectional illustration of two pairs of conductive traces configured to measure resistance of a skin barrier adhesive, wherein R1 is resistance between a first pair of conductive traces and R2 is resistance between a second pair of conductive traces. In the embodiment of FIG. 2, the leakage detection system may be configured to determine a leakage event from a decrease in resistance R2 between the second pair of conductive traces upon exposure to ostomy effluent.

Figure 3:
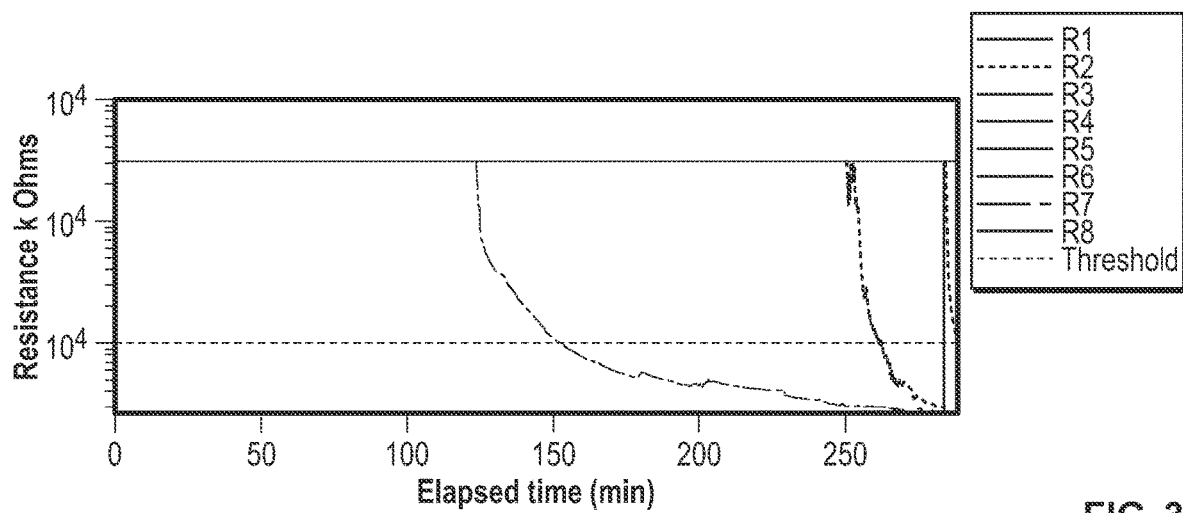
FIG. 3 is a graph of resistance measured by a sensing accessory according to an embodiment.

FIG. 3 is a graph displaying resistance data collected from a sensing accessory comprising a plurality of sensors according to an embodiment, wherein a drop of resistance is recorded at multiple sensors as a leakage progresses outward and contacts different sensors. As shown, the resistance drops from a value exceeding a measurement range of a processor (>2 MΩ) to very low (approximately 1 kΩ). In this embodiment, the resistance of the sensors may be negligible when compared to the large magnitude of a resistance change upon exposure to ostomy fluid. Thus, the sensors for the sensing accessory may be formed from conductive traces of various thicknesses and arrangements as long as the resistance of the conductive trace is low relative to the baseline (dry) resistance between the conductive traces.

In an embodiment, the sensing accessory 12 may include a plurality of conductive traces as shown in FIG. 4 and FIG. 5A-5C. Each of the conductive traces may be configured to have a width of about 0.002 inches and arranged spaced apart from each other with a gap of about 0.002 inches. In other embodiments, the conductive traces may be configured wider or narrower and arranged in various configurations. In an embodiment, the gap between the conductive traces may be about 0.01 inches. In an embodiment, a plurality of radially spaced layers of conductive traces may be configured and arranged to fit within a space defined by an ostomy pouch system barrier.

Figure 4:
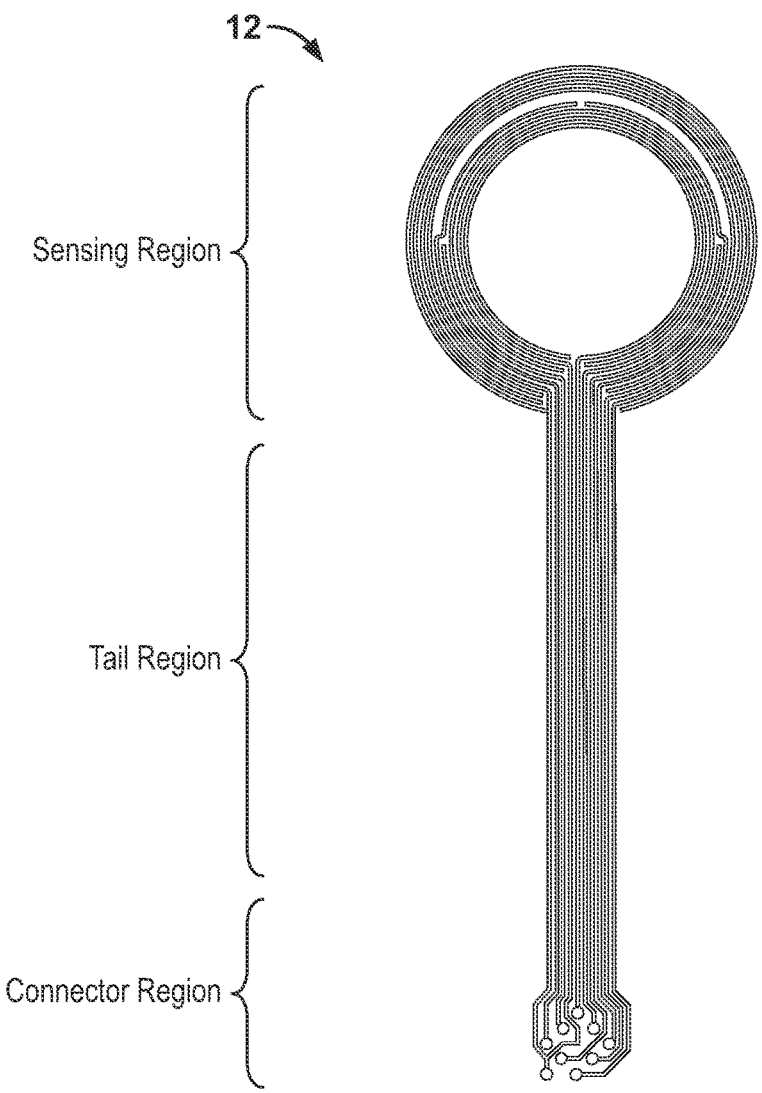
FIG. 4 is a schematic illustration of leakage sensors comprising a plurality of conductive traces according to an embodiment.
Figure 5C:
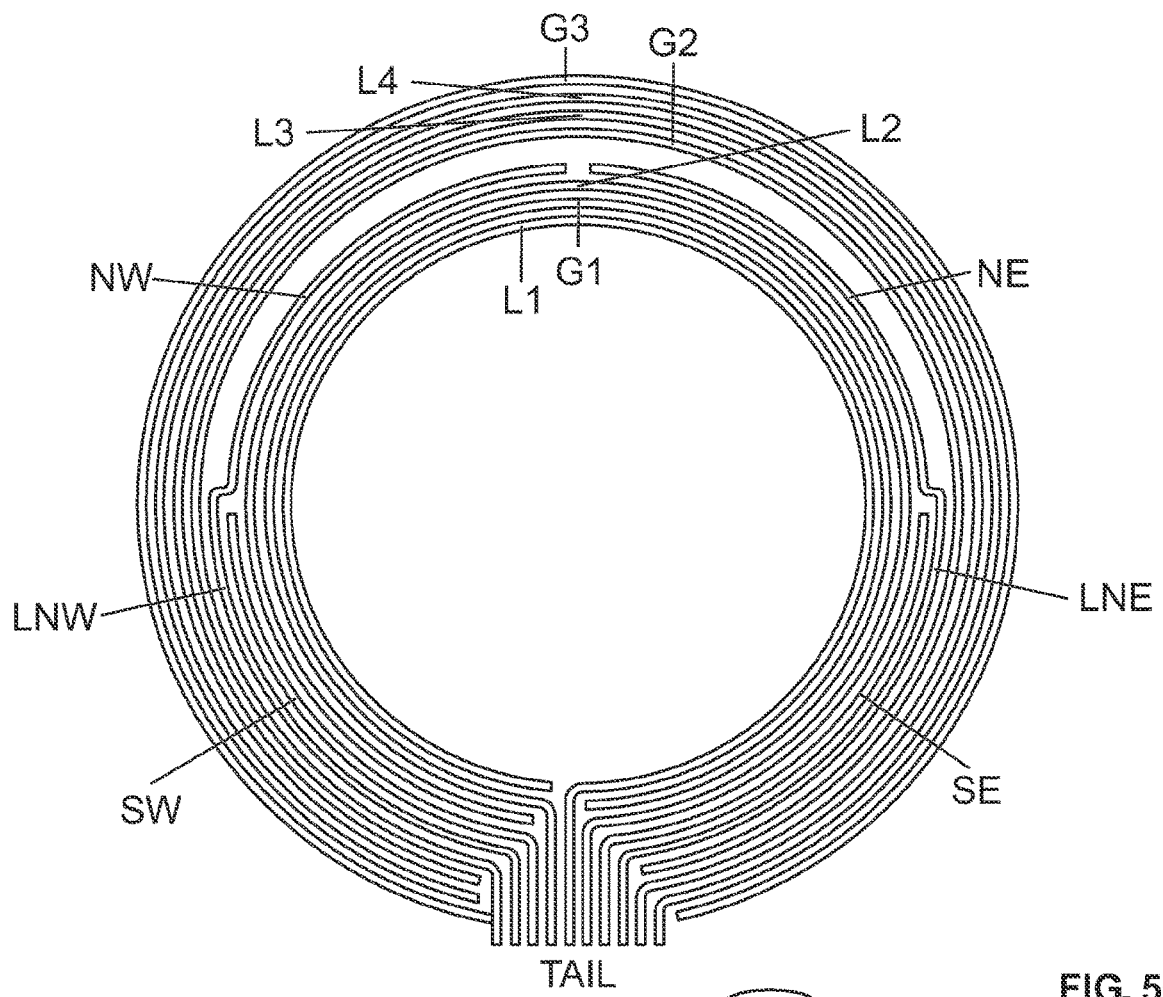

The sensing accessory 12 may comprise a plurality of sensors formed from a plurality of substantially elliptical conductive traces arranged around a center opening for receiving a stoma. "Substantially elliptical conductive traces" as used herein include conductive traces having various elliptical shapes, such as circular, oval, etc. Each of the plurality of sensors may be arranged at different radial distances from the center opening. Each sensor may cover a portion of the area surrounding the central opening. In the embodiment of FIG. 4 and FIGS. 5A-5C, the sensors may be arranged in five layers at different radial distances. Four sensor layers are labeled L1, L2, L3, and L4 as best shown in FIGS. 5A and 5C. Each of the four layers L1, L2, L3, and L4 may be configured to substantially surround the center opening, such that a leakage in any radial direction may be detected. The plurality of sensors may also include three ground traces G1, G2, G3, wherein G1 is arranged between L1 and L2, G2 is arranged between a fifth sensor and L3, and G3 is arranged adjacent L4 as best shown in FIGS. 5A and 5C. In such an embodiment, the sensing accessory 12 may be configured to measure resistance between L1 and G1 (first level sensor), between L2 and G1 (second level sensor), between G2 and L3 (third level sensor), and between L4 and G3 (fourth level sensor).

In this embodiment, the fifth sensor layer may be arranged between L2 and G2 and may be subdivided into four quadrants SW, NW, NE, and SE, which corresponds to intercardinal directions with a tail of the sensing accessory 12 oriented at South as shown in FIGS. 5A and 5C. The four quadrants may be evenly spaced at about 90 degrees, each quadrant covering about quarter of the area around the center opening. In this embodiment, a lower portion of NW sensor (LNW), a lower portion of NE sensor (LNE), and tail portions of the sensors and ground traces may be covered with a masking layer as best shown in FIG. 5B. In other embodiments, the fifth layer may comprise more than four or less than four subdivisions and/or unevenly divided subdivisions. The fifth sensor layer comprising subdivided sensor sections may be configured to detect a radial direction of a leakage according to a change in resistance measured at one or more of the subdivisions. The sensors arranged at different radial distances may be configured to track a progression of ostomy effluent leakage. By only subdividing some layers, the total number of sensors may be reduced while preserving the location-detection function.

In an embodiment, the conductive traces may be printed on a circuit substrate using a conductive ink. Suitable materials for the circuit substrate may include, but are not limited to polyester (PET), polyethylene (PE), polyurethane film (PU), or thermoplastic polyurethane (TPU) film. The circuit substrate may be configured to provide an excellent bonding surface for the conductive ink, prevent mechanical damage to the conductive ink, and adhere to hydrocolloid adhesive layer. In some embodiments, the circuit substrate and the conductive ink may be configured to provide at least some degree of elasticity to allow stretching of the sensing accessory 12. In an embodiment, the sensing accessory 12 may comprise a PET circuit substrate having a thickness of about 0.001 inches to about 0.010 inches, preferably about 0.003 inches.

In some embodiments, the sensing accessory 12 may include masking layers covering some portions of the conductive traces. The masking layers may be formed from a film or a masking material. The masking layer may be configured to prevent bridging of the conductive traces by fluid in the covered portions. In an embodiment, a making layer may cover a tail region of the conductive traces. The making layer may extend into a portion of sensors and connector regions. In the embodiment of FIGS. 5A-5C, lower portions of the NW and NE sensors (LNW, LNE) may be covered by masking layers, which allows for leakage detection only in the exposed portions of the sensors. The tail portion may be masked to prevent false leak detection resulting from sensors being bridged by fluid outside of an ostomy skin barrier area. FIG. 5A illustrates exposed portions of the conductive traces of the sensing accessory 12, while FIG. 5B illustrates masked portions of the conductive traces. In some embodiments, the masking layer may be configured to promote adhesion between a hydrocolloid adhesive layer of a skin barrier and the sensing accessory 12.

The sensing accessory 12 may be configured to be compatible with existing ostomy appliances and to adapt to various stoma sizes and shapes. A center opening of the sensing accessory 12 may be configured to align with an opening in an ostomy barrier to receive a stoma. When the sensing accessory 12 is placed on the ostomy barrier, a backing layer of the sensing accessory may be attached to a hydrocolloid layer of the ostomy barrier. The backing layer may be formed from a suitable material, such as an adhesive, a dead-stretch film, etc. The backing layer may be configured to allow a user to adapt the shape of the center opening, for example, by cutting or molding, to fit a stoma. The backing layer may be provided with labels to guide and limit cutting or shaping of the sensing accessory 12 to prevent damaging of the sensing accessory circuitry.

In some embodiments, the sensing accessory 12 may be configured to be molded to conform to the convexity of a convex ostomy barrier. In an embodiment, the sensing accessory 12 may comprise a stretchable printed circuit system to conform to a convex ostomy barrier. In such an embodiment, a circuit substrate, printed conductive traces, and masking layers may be formed from stretchable materials, such as the Dupont INTEXAR system. In another embodiment, the sensing accessory may include slits and voids configured and arranged in a non-stretchable circuit substrate, such as PET, to conform the sensing accessory to a convex barrier.

The sensing accessory 12 may include a hydrocolloid adhesive layer to provide an interface between an ostomy pouch system and user's skin. The adhesive may be configured similar to known hydrocolloid adhesives on ostomy products—e.g. absorbing fluid while maintaining adhesion to the skin. The adhesive may be configured to change conductivity upon exposure to fluid to enable leakage detection by measuring the conductivity or resistance of the adhesive. In an embodiment, the sensing accessory 12 may include a hydrocolloid adhesive layer configured to exhibit a resistance drop from greater than 2 M$\Omega$ to about 1 k$\Omega$ when the hydrocolloid adhesive layer absorbs ostomy effluent. The adhesive may also be configured to have other desirable properties, such as pH balancing or infusion of skin-friendly ingredients.

Figure 6:
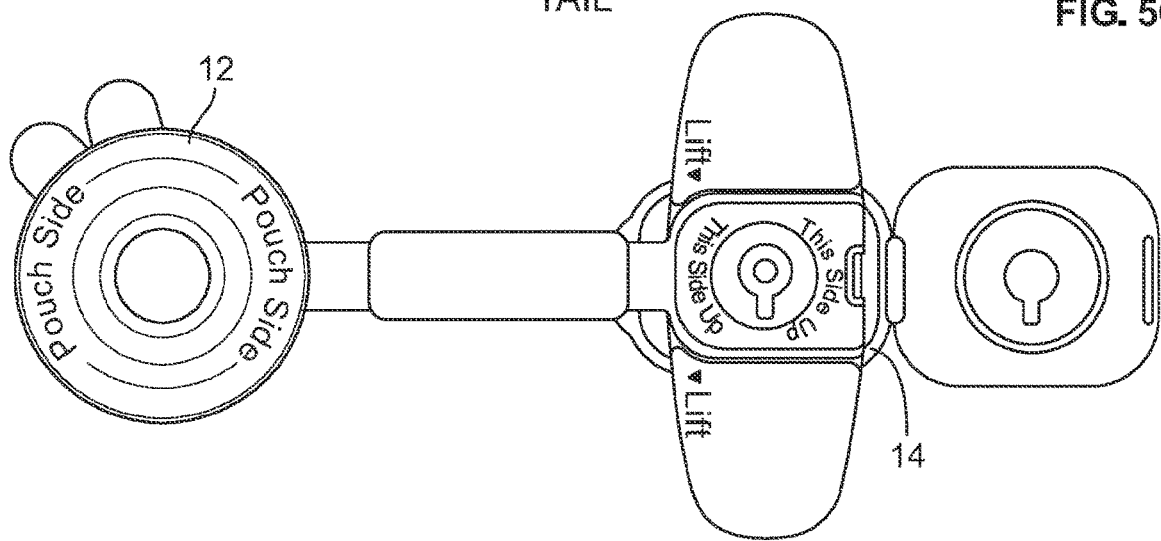
FIG. 6 is a perspective illustration of a sensing accessory engaged with a wearable subsystem according to an embodiment.

The adhesive layers of the sensing accessory 12 may be covered by release liners. The release liner may be formed from a silicone-coated film and may include a tab to facilitate removal. In an embodiment, the sensing accessory 12 may include two release liners, each covering opposing surfaces of the sensing accessory 12. The release liners may be arranged such that the release liner tabs may be offset as shown in FIG. 6. Alternatively, the release liners may be arranged such that the tabs may be aligned, wherein one tab may be bigger than the other to facilitate a correct order of removal. In the embodiment of FIG. 6, the release liners may be labeled to guide a user through removal of the release liners, assembling of the sensing accessory with an ostomy pouch system, and attaching the assembled sensing accessory and ostomy pouch system to user's body.

The sensing accessory 12 may be manufactured through progressive assembly of constituent materials. At least some of the materials, for example, a circuit substrate, tail cover, release liners, etc., may be provided in a roll form and processed and cut into shape, for example, by die-cutting, for assembly. The hydrocolloid adhesive may be extruded into a roll having a specified thickness, which may be cut in line and assembled. Alternatively, the hydrocolloid adhesive may be molded on top of the assembled circuit, then cut to shape.

Figure 7:
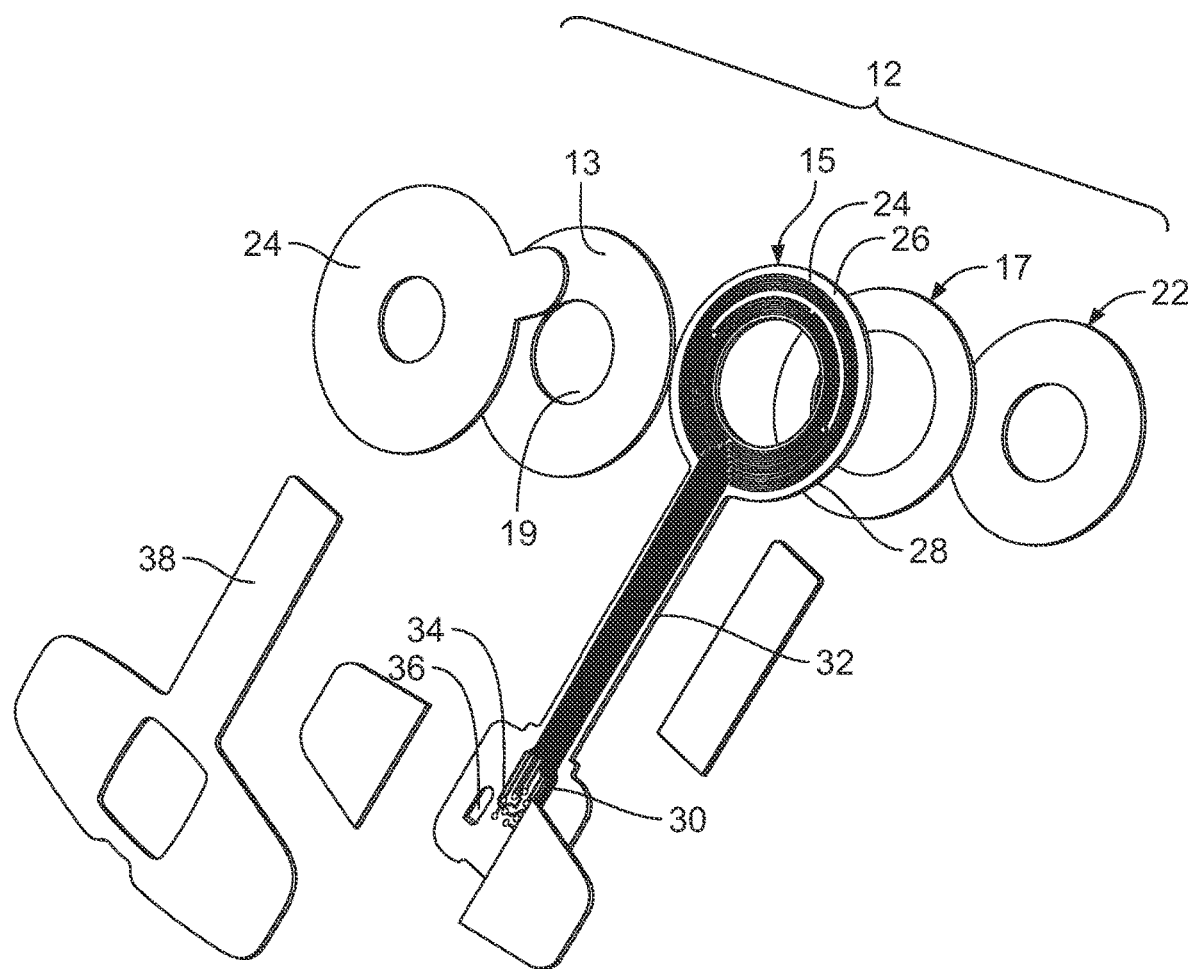
FIG. 7 is an exploded view of a sensing accessory according to an embodiment.

The sensing accessory 12 may be coupled to the wearable subsystem 14. The conductive traces, which form the sensors, may extend beyond the periphery of an ostomy skin barrier and to a connector region configured to engage the wearable subsystem 14. The portion of the sensing accessory 12 that extends between a sensor region and the connector region is referred to herein as a tail or tail region as shown in FIGS. 4 and 7. Selecting a flexible substrate for the sensing accessory 12 may allow a user to position the wearable subsystem 14 in a variety of locations on their skin, ostomy pouch, or clothing.

A layout of the terminating sections of the conductive traces may be configured to correspond to conductive connecting sections of the wearable subsystem 14. This allows an electrical connection to be formed between the conductive traces of the sensing accessory 12 and a processor of the wearable subsystem 14. FIGS. 5A, 5B and 7 illustrate an embodiment of a sensing accessory connector region comprising two openings in the substrate, which function as alignment members corresponding to raised alignment members of a wearable subsystem 14. The alignment members may be configured to facilitate correct alignment and connection between the sensing accessory 12 and the wearable subsystem 14.

FIG. 7 shows an exploded view of the sensing accessory 12 according to an embodiment. The sensing accessory 12 may generally comprise an adhesive layer 13, a sensor layer 15 and a barrier-side layer (also referred to herein as a backing layer) 17. A center opening 19 configured to receive a stoma may extend through the sensing accessory 12. The center opening 19 may be formed by respective openings provided in individual layers of the sensing accessory 12. Each layer 13, 15, 17 of the sensing accessory 12 may have a proximal side and a distal side. When the sensor accessory 12 is attached to a user, the respective proximal sides generally face the user and the respective distal sides generally face away from the user.

The adhesive layer 13 may be disposed on a body-side of the sensing accessory 12. In an embodiment, the proximal side of the adhesive layer 13 may form at least a portion of the body-side surface of the sensor accessory 12. The proximal side of the adhesive layer 13 may be configured to adhere to the peristomal skin surface of a user and seal around the stoma. The adhesive layer 13 may be formed from a medical-grade pressure sensitive adhesive that can adhesively secure the sensing accessory 12 to the user. In an embodiment, the adhesive layer 13 may be formed from a hydrocolloid adhesive. A release liner 21 may be provided on the proximal side of the adhesive layer 13 to cover the adhesive, which may be removed before attaching the sensing accessory 12 to user's skin.

The barrier-side layer 17 may be formed from a flexible material that is generally soft and non-irritable to user's skin, such as an adhesive, polymeric film, nonwoven or foam material. In an embodiment, the barrier-side layer 17 may be formed from an adhesive, such as a hydrocolloid adhesive. In such an embodiment, a release liner 22 may be provided on the distal side of the barrier-side layer 17 to cover the adhesive, which may be removed before applying the sensing accessory 12 to an ostomy barrier or faceplate.

The sensor layer 15 may include sensors formed from an electrically conductive circuitry 24, such as a plurality of electrodes, conductive traces or the like. The electrically conductive circuitry 24 may be disposed on a circuit substrate 26. In an embodiment, the sensor layer 15 may include a sensor region 28, a connector region 30 and a tail region 32 arranged therebetween. The electrically conductive circuitry 24 may be arranged in a predetermined pattern in the sensor region 28. For example, the electrically conductive circuitry 24 may be generally arranged in a circular or semi-circular pattern. Other suitable patterns are envisioned as well, such as an oval or oblong pattern, or other closed or substantially closed loop pattern. The electrically conductive circuitry 24 in the sensor region 28 may be arranged at one or more radial distances from the center opening 19. For example, the conductive circuitry 24 may comprise a plurality of electrically conductive traces arranged at a plurality of different, radial distances from the center opening 19.

In an embodiment, the tail region 32 may generally be formed as an elongated section extending from the sensor region 28 to the connector region 30. The tail region 32 may extend beyond an outer periphery of the first adhesive layer 13 and/or the barrier-side layer 17 in a direction radially outward from the center opening 19. The electrically conductive circuitry 24 may extend along the tail region 32. In an embodiment, the tail region 32 may be flexible along at least a portion of its length such that it may be folded or wrapped.

The connector region 30 may include a plurality of connection points 34 electrically connected to the conductive circuitry 24. The connection points 34 may include an externally accessible portion configured for electrical connection to an external device, such as the wearable subsystem 14. In this manner, the connection points 34 may provide an electrical connection between the wearable subsystem 14 and the electrically conductive circuitry 24. The externally accessible portion of the connection points 34 may be any suitable electrical interface for forming an electrical connection between two electrical components, such as one or more electrically conductive contacts, pins, and the like.

The connector region 30 may also include one or more alignment members 36. The one or more alignment members 36 may be configured to engage corresponding alignment members of the wearable subsystem 14 to facilitate positioning of the connector region 30 relative to the wearable subsystem 14 to ensure electrical connection therebetween. In an embodiment, the one or more alignment members 36 of the connector region 30 may be an opening, recess or slot. The corresponding alignment members of the wearable subsystem 14 may be one or more projections configured for receipt in the opening, recess or slot of the connector region 30.

In an embodiment, the sensing accessory 12 may be configured to detect a leakage by measuring resistance between electrodes. For example, the sensing accessory 12 may be configured to detect a change in resistance between electrodes triggered by ostomy effluent bridging the electrodes as a leakage propagates. In the embodiment of FIG. 7, the electrically conductive circuitry 24 may comprise a plurality of electrodes arranged on the proximal side of the sensor region 28, such that the electrodes may be positioned adjacent and in contact with the adhesive layer 13 to measure resistance of the adhesive layer 13. The plurality of electrodes 24 may extend along the proximal side of the tail region 32 and along a portion of the connector region 30 to the connection points 34. In such an embodiment, a masking element may be used to prevent shorting between electrodes in the areas where detection is not desired. For example, a masking element 38 may be provided on the body-side of the sensing accessory 12 to cover the plurality of electrodes 24 in the tail region 32.

FIG. 22 is a schematic illustration of the sensing accessory 12 attached to an ostomy barrier 20 and fitted around a stoma 2 according to an embodiment. The sensing accessory 12 may be configured such that a first conductive trace or electrode 25 of the electrically conductive circuitry 24 may be arranged adjacent a center opening 19 with a minimum space therebetween of about 0.25 inches to allow for fitting around the stoma 2 without damaging the electrically conductive circuitry 24.

Figure 8:
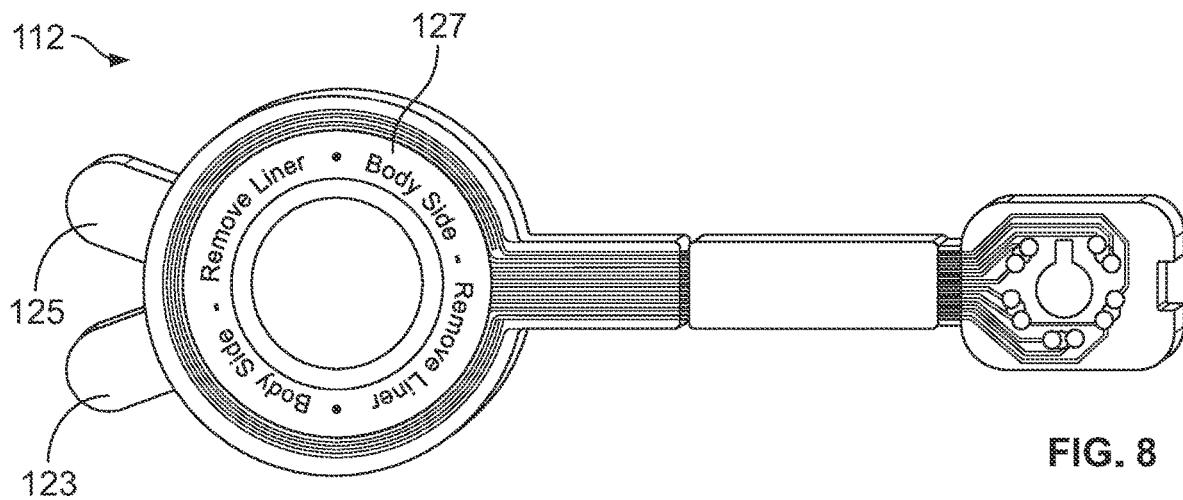
FIG. 8 is a perspective illustration of a sensing accessory according an embodiment.
Figure 9:
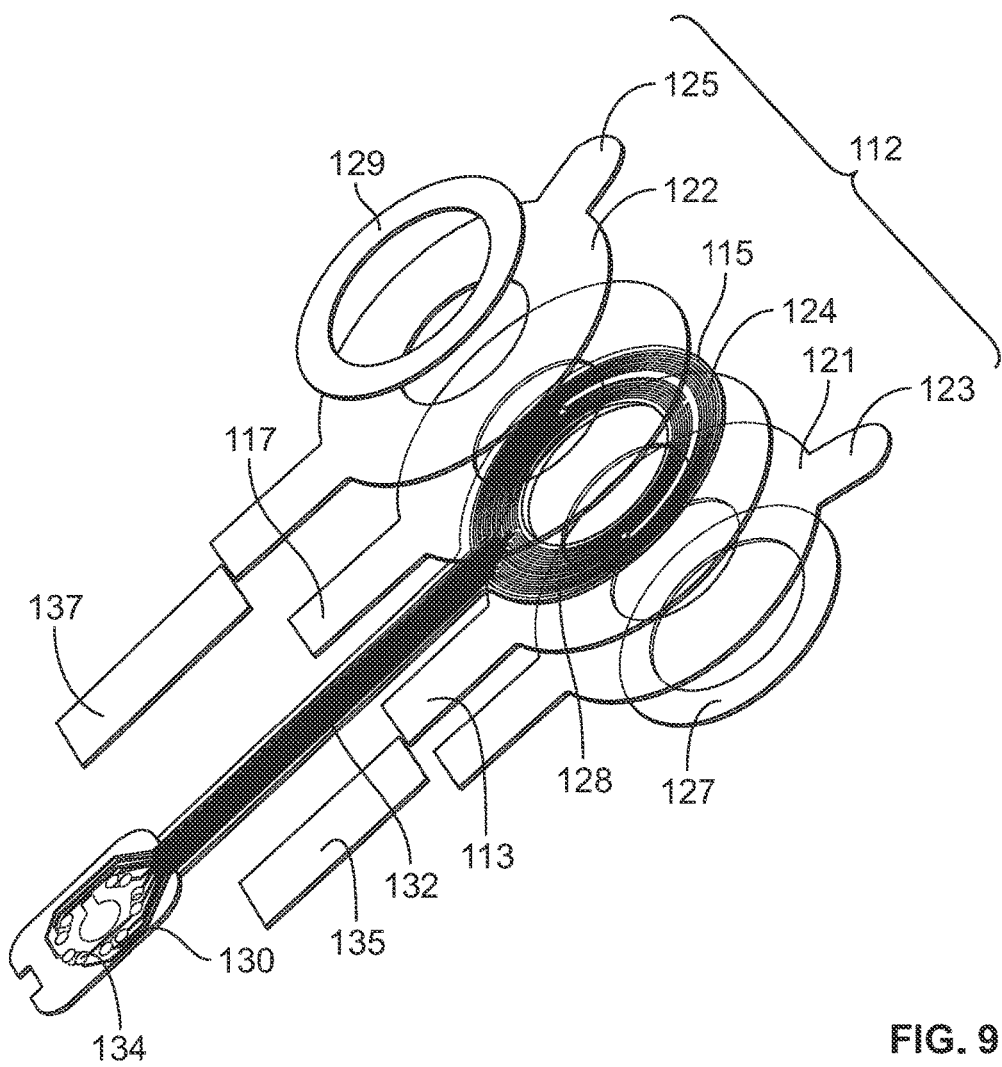
FIG. 9 is an exploded view of the sensing accessory of FIG. 8.

FIGS. 8 and 9 illustrate a sensing accessory 112 according to another embodiment. The sensing accessory 112 may be configured similar to the sensing accessory 12, generally comprising an adhesive layer 113, a sensor layer 115 and a barrier-side layer 117. The adhesive layer 113 may be formed from a hydrocolloid adhesive and disposed on a body-side of the sensing accessory 112 for attachment to a user. A release liner 121 including a tab 123 may be provided on the proximal side of the adhesive layer 113. The barrier-side layer 117 may be formed from an adhesive, and a release liner 122 including a tab 125 may be provided on a distal side of the barrier-side layer 117. The release liners 121, 122 may be arranged such that the tabs 123, 125 are offset from each other as best shown in FIG. 8. Indicator labels 127, 129 may be provided on each side of the sensing accessory 112 to guide assembling of the sensing accessory 112 with an ostomy appliance and attachment of the same to a user.

The sensor layer 115 may comprise a generally ring-shaped sensor region 128, a connector region 130 and a tail region 132 connecting the sensor region 128 and the connector region 130. The sensor region 128 may comprise sensors formed from an electrically conductive circuitry 124, which may extend through the tail region 132 and to connection points 134 in the connector region 130. The tail region 132 may be formed as an elongated section extending between the sensor region 128 and the connector region 130. The connection points 134 may be configured to electrical connect the sensing accessory 112 to an external device, such as the wearable subsystem 14. The exposed portions of the tail region 132 that are not covered by the adhesive layer 113 and the barrier-side layer 117 may be covered by tail covers 135, 137.

Figure 10:
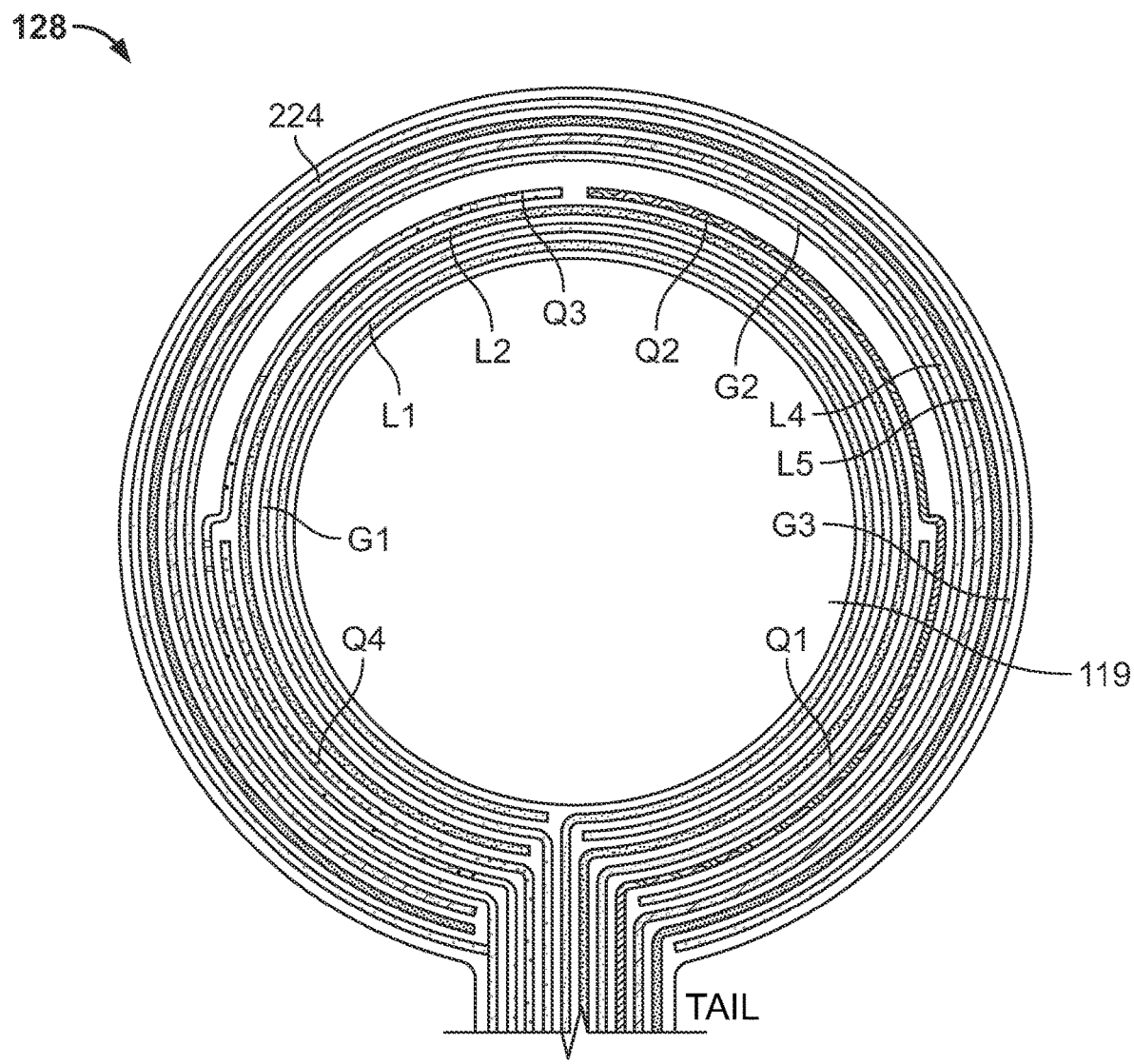
FIG. 10 is a schematic illustration of leakage sensors comprising a plurality of conductive traces according to an embodiment.

FIG. 10 illustrates an electrically conductive circuitry 224 arranged on a proximal side of the sensor region 128 according to an embodiment. The electrically conductive circuitry 224 may comprise a plurality of substantially circular conductive traces, also referred to herein as circular electrodes, L1, L2, L4, L5, G1, G2, G3, and a plurality of arc shaped conductive traces, also referred to herein as electrode arcs, Q1, Q2, Q3, Q4. Each of the circular electrodes may be arranged at a different radial distance from a center opening 119 and configured to determine a radial progress of ostomy effluent leakage.

In this embodiment the electrically conductive circuitry 224 may include four electrode arcs arranged in different sections of the sensor region 128 to determine a location of a leak in the sensor region 128. A first electrode arc Q1 may be arranged to extend along a southeast (SE) quadrant of the sensor region 128. A second electrode arc Q2 may be arranged to extend along an east half of the sensor region 128, wherein a lower portion of the second electrode arc Q2 that extends adjacent the first electrode arc Q1 may be covered with a making layer (similar to the masked LNE shown in FIG. 5B), such that the exposed portion the second electrode arc Q2 only extends along a northeast (NE) quadrant of the sensor region 128. A third electrode arc Q3 may be arranged to extend along a west half of the sensor region 128, wherein a lower portion of the third electrode arc Q3 that extends adjacent a fourth electrode arc Q4 may be covered with a making layer (similar to the masked LNW shown in FIG. 5B), such that the exposed portion the third electrode arc Q3 only extends along a northwest (NW) quadrant of the sensor region 128. The fourth electrode arc Q4 may be arranged to extend along a southwest (SW) quadrant of the sensor region 128. In this embodiment, a change in electrical resistance measured by one of the four electrode arcs may be used to determine the location of a leakage. In other embodiments, the electrically conductive circuitry 224 may include less than four electrode arcs or more than four electrode arcs, which may be arranged in different sections of the sensor region 128 and configured to identify a leakage location.

In the embodiment of FIG. 10, the circular electrodes may comprise four level sensors L1, L2, L4, L5 and three ground electrodes G1, G2, G3, wherein resistance measured between a level sensor and a ground electrode may be analyzed to determine a leakage. In this embodiment, first and second level sensors L1, L2 may share a first ground electrode G1, wherein resistance measured between a first lever sensor L1 and the first ground electrode G1 may be analyzed to determine a level 1 leakage, and resistance measured between the first ground electrode G1 and a second level sensor L2 may be analyzed to determine a level 2 leakage. A second ground electrode G2 may be shared between the electrode arcs Q1, Q2, Q3, Q4 and a fourth level sensor L4, wherein resistance measured between the electrode arcs Q1, Q2, Q3, Q4 and the second ground electrode G2 may be analyzed to determine a level 3 leakage at a specific quadrant, and resistance measured between the second ground electrode G2 and the fourth level sensor L4 may be analyzed to determine a level 4 leakage. A level 5 leakage, which is the most critical leakage level in this embodiment, may be determined by analyzing resistance measured between a fifth level sensor L5 and a third ground electrode G3.

Figure 11:
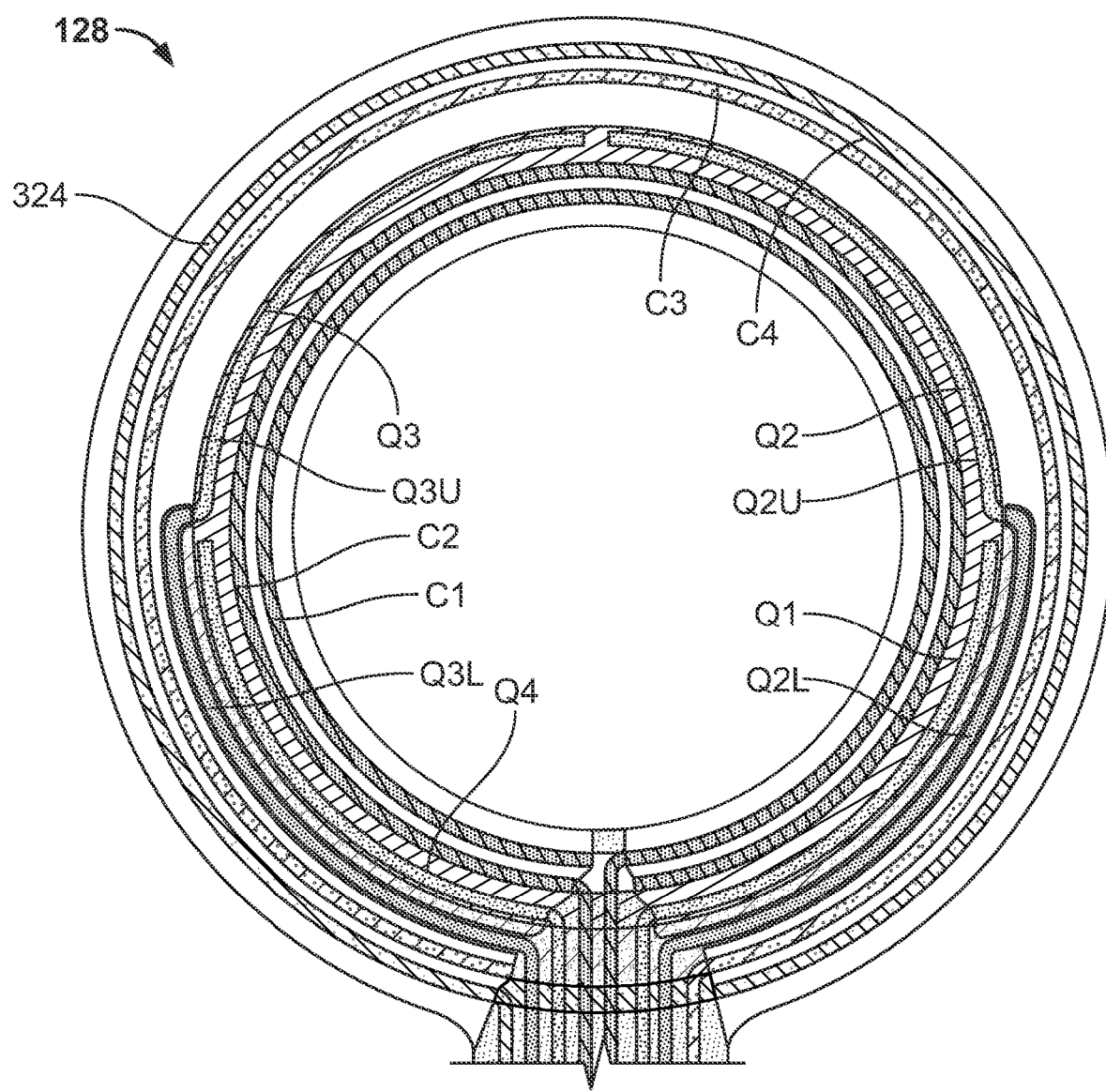
FIG. 11 is a schematic illustration of leakage sensors comprising a plurality of conductive traces according to another embodiment.

FIG. 11 illustrates an electrically conductive circuitry 324 arranged on a proximal side of the sensor region 128 according to another embodiment. The electrically conductive circuitry 324 may comprise a plurality of substantially circular conductive traces C1, C2, C3, C4, and a plurality of arc shaped conductive traces Q1, Q2, Q3, Q4. In this embodiment the electrically conductive circuitry 324 may include four electrode arcs arranged in different sections of the sensor region 128 to determine a location of a leak in the sensor region 128. A first electrode arc Q1 may be arranged to extend along a SE quadrant of the sensor region 128. A second electrode arc Q2 may be arranged to extend along an east half of the sensor region 128, wherein an upper portion Q2U extends along a NE quadrant of the sensor region 128 and a lower portion Q2L, which may be masked, extends along a SE quadrant of the sensor region 128. A third electrode arc Q3 may be arranged to extend along a west half of the sensor region 128, wherein an upper portion Q3U extends along a NW quadrant of the sensor region 128 and a lower portion Q3L, which may be masked, extends along a SW quadrant of the sensor region 128. A fourth electrode arc Q4 may be arranged to extend along a southwest (SW) quadrant of the sensor region 128.

In this embodiment, a change in resistance measured between a first circular electrode C1 and a second circular electrode C2 may be analyzed to determine a level 1 leakage. A change in resistance measured between the second circular electrode C2 and the first electrode arc Q1 may be analyzed to determine a level 2 leakage in the SE quadrant. A change in resistance measured between the second circular electrode C2 and the upper portion of the second electrode arc Q2U may be analyzed to determine a level 2 leakage in the NE quadrant. A change in resistance measured between the second circular electrode C2 and the upper portion of the third electrode arc Q3U may be analyzed to determine a level 2 leakage in the NW quadrant. A change in resistance measured between the second circular electrode C2 and the fourth electrode arc Q4 may be analyzed to determine a level 2 leakage in the SW quadrant. A change in resistance measured between the first electrode arc Q1 and a third circular electrode C3 may be analyzed to determine a level 3 leakage in the SE quadrant, wherein a detection algorithm may set a higher threshold for leakage detection to compensate for a greater distance between the first electrode arc Q1 and the third circular electrode C3. A change in resistance measured between the upper portion of the second electrode arc Q2U and the third circular electrode C3 may be analyzed to determine a level 3 leakage in the NE quadrant. A change in resistance measured between the upper portion of the third electrode arc Q3U and the third circular electrode C3 may be analyzed to determine a level 3 leakage in the NW quadrant. A change in resistance measured between the fourth electrode arc Q4 and the third circular electrode C3 may be analyzed to determine a level 3 leakage in the SW quadrant, wherein a detection algorithm may set a higher threshold for leakage detection to compensate for a greater distance between the first electrode arc Q4 and the third circular electrode C3. A change in resistance measured between the third circular electrode C3 and a fourth circular electrode C4 may be analyzed to determine a level 4 leakage.

Wearable Subsystem

Figure 12:
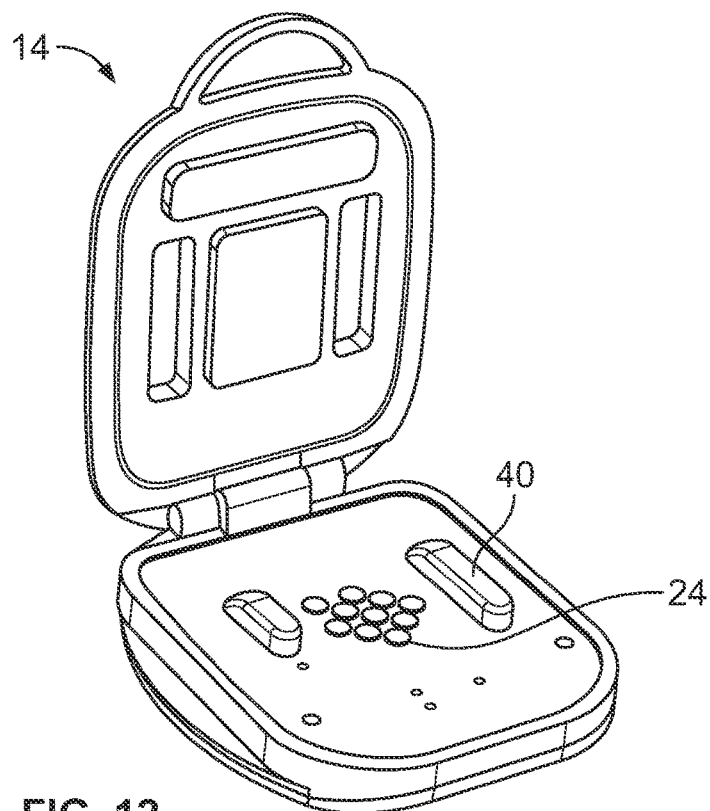
FIG. 12 is a perspective illustration of a wearable subsystem according to an embodiment.
Figure 13:
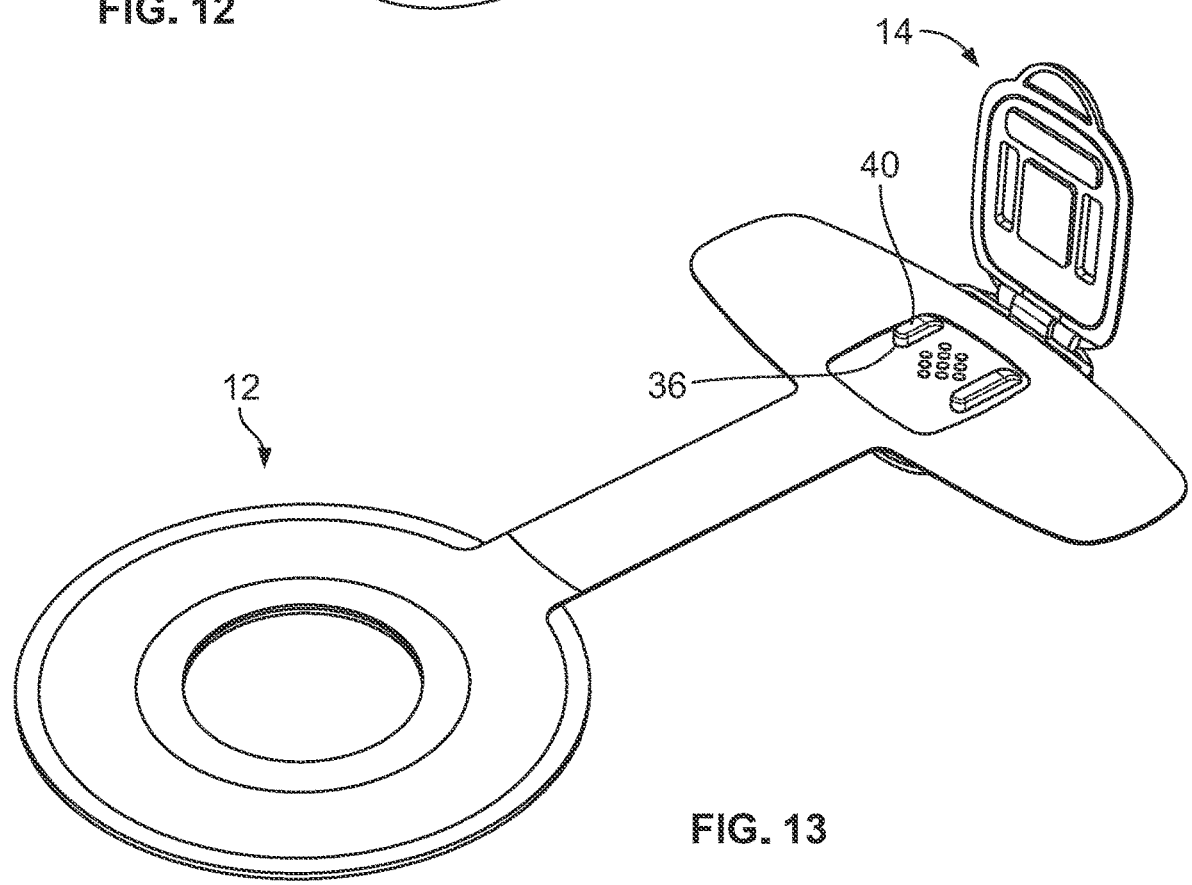
FIG. 13 is a perspective illustration of the wearable subsystem of FIG. 12 connected to a sensor accessory according to an embodiment.

The wearable subsystem 14 may function as a relay between the sensing accessory 12 and a user or other subsystems of the leakage detection system 10. The wearable subsystem 14 may be configured to physically and electronically connect to the sensing accessory 12 and receive and analyze signals from the sensing accessory 12. The wearable subsystem 14 according to an embodiment is shown in FIGS. 12 and 13. The wearable subsystem 14 may comprise a hinged case, an imbedded circuit board, a battery, a motor, and alignment members 40 that correspond to alignment members 36 of the sensing accessory 12. The circuit board may include conductive members 24 configured to contact terminal ends of sensing traces of the sensing accessory 12, such as the connecting points 34 (FIG. 7). In this embodiment, the conductive members 24 comprising a plurality of raised conductive pads may be arranged generally in a center area of a bottom housing of the wearable subsystem 14.

The alignment members 40 may comprise two raised members, each of which may be arranged on each side of the conductive members 24 as shown in FIG. 12. In such an embodiment, the alignment members 36 of the sensing accessory 12 may be defined by two openings in the connector region 30, which may be configured to receive the raised alignment members 40 of the wearable subsystem 14. The alignment members 36, 40 may be configured to facilitate correct attachment of the wearable subsystem 14 to the sensing accessory 12 to ensure electrical connection therebetween. A user may form a connection between the sensing accessory 12 and the wearable subsystem 14 by aligning the corresponding alignment members 36, 40 as shown in FIG. 13 and closing the wearable subsystem 14.

Figures 14, 15:
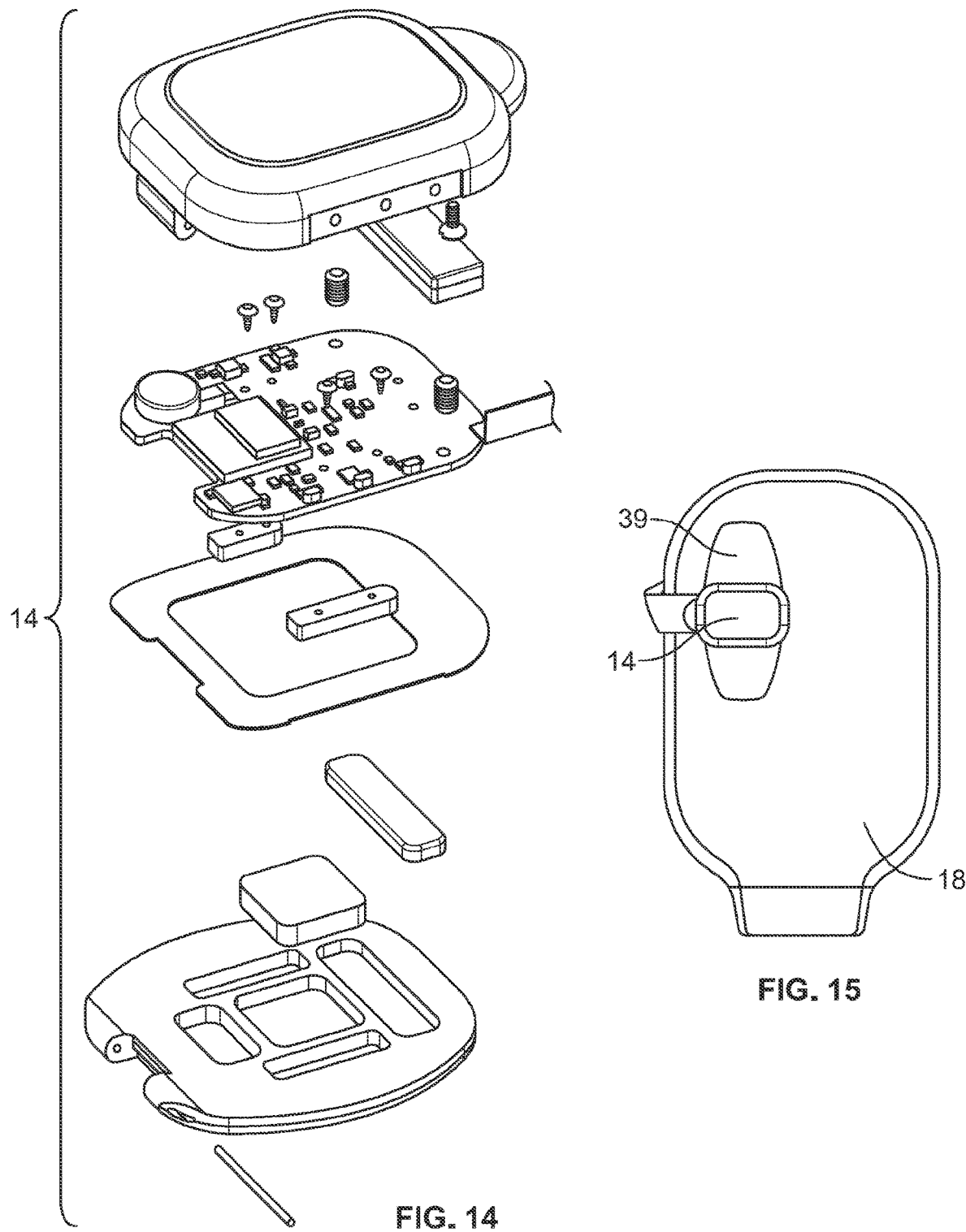
FIG. 14 is an exploded view of a wearable subsystem according to an embodiment.
FIG. 15 is a perspective illustration of a wearable subsystem and a sensor accessory attached to an ostomy pouch appliance according to an embodiment.

The circuit board of the wearable subsystem 14 may include a processor and other components to analyze signals received from the sensing accessory 12, communicate with external devices, such as a mobile device and a charging dock 16, and alert a user vis sound, vibration, LEDs, etc. to notify a system status. FIG. 14 is an exploded view of a wearable subsystem 14 according to an embodiment.

In an embodiment, the wearable subsystem 14 may be secured to an ostomy pouch 18 or user via adhesive pads 39 attached to the sensing accessory 12 as shown in FIG. 15. The adhesive pads 39 may be covered with release liners, which may be removed before use.

Figure 16:
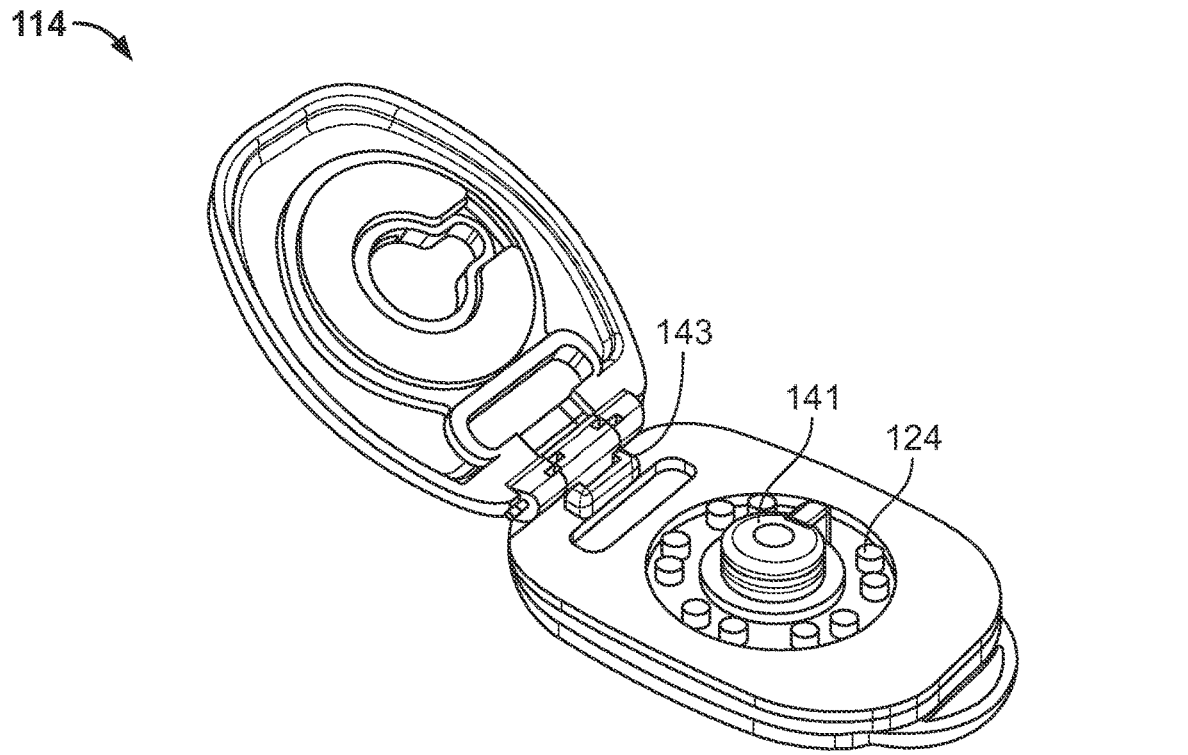
FIG. 16 is a perspective illustration of a wearable subsystem according to an embodiment.
Figure 17:
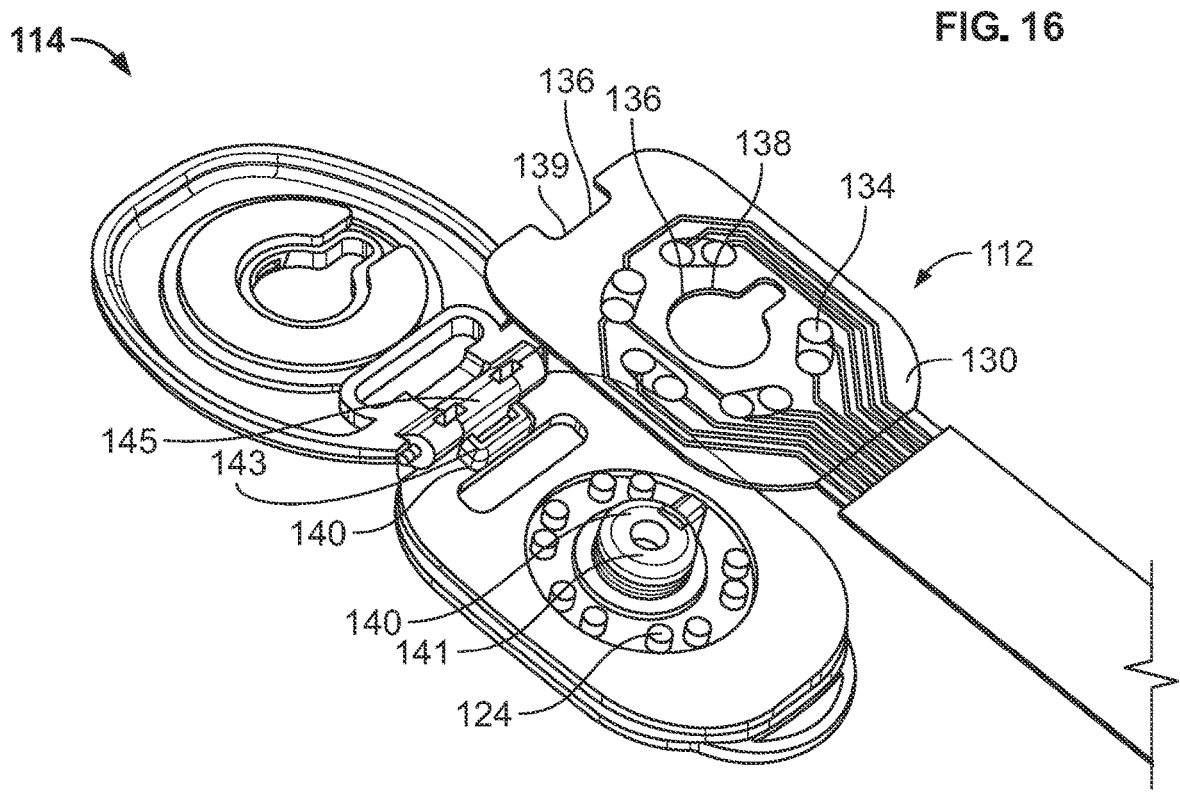
FIG. 17 is a perspective illustration of the wearable subsystem of FIG. 16 and a connector region of a sensing accessory configured to engage the wearable subsystem according to an embodiment.
Figure 18:
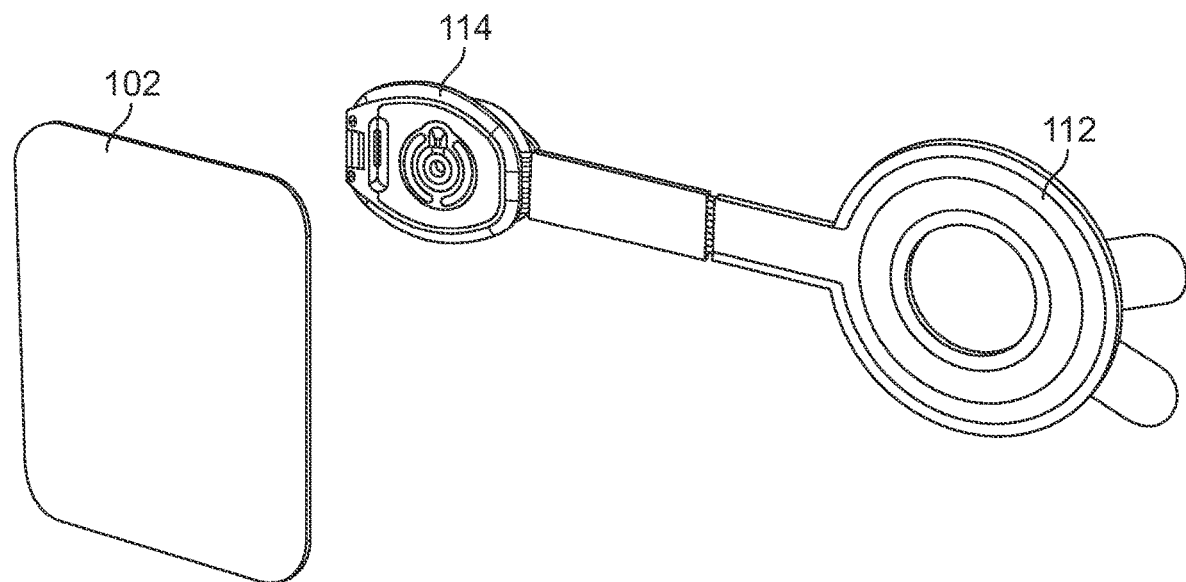
FIG. 18 is a perspective illustration of the wearable subsystem and the sensing accessory of FIG. 17 and an adhesive pad for attaching the wearable subsystem to a user or an ostomy pouch appliance according to an embodiment.
Figures 19, 20, 21:
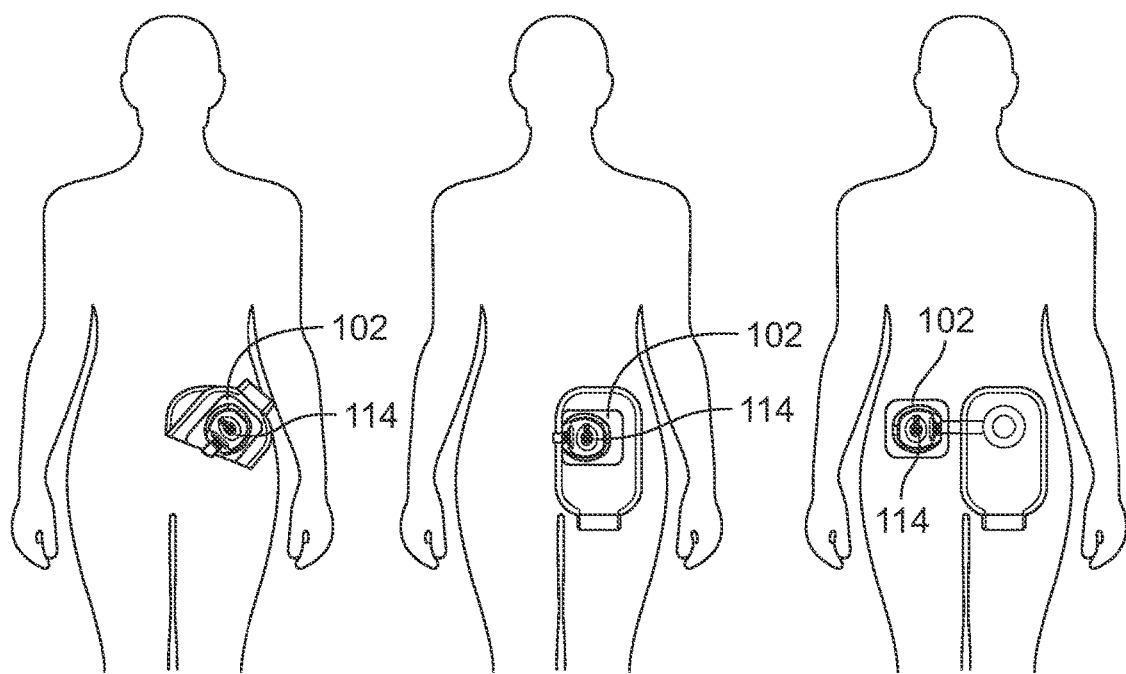
FIG. 19 is an illustration of a wearable subsystem attached to a body-side of an ostomy pouch appliance according to an embodiment.
FIG. 20 is an illustration of a wearable subsystem attached to a distal-side of an ostomy pouch appliance according to an embodiment.
FIG. 21 is an illustration of a wearable subsystem attached to a user according to an embodiment.

FIGS. 16 and 17 show a wearable subsystem 114 according to another embodiment. The wearable subsystem 114 may be configured similar to the wearable subsystem 14, generally comprising a hinged case, an imbedded circuit board, a battery, a motor, and an alignment member 140 that correspond to an alignment member 136 of the sensing accessory 112. The circuit board may include conductive members 124 configured to contact the connecting points 134 of the sensing accessory 112.

In this embodiment, the wearable subsystem alignment member 140 may comprise a center raised key member 141 and a peripheral raised member 143. The center raised key member 141 may be arranged generally in the center of a bottom housing of the wearable subsystem 114, while the peripheral raised member 143 may be arranged proximate a hinge 145. The alignment member 136 of the sensing accessory 112 may be defined by openings in the connector region 130, which may be configured to receive the raised alignment member 140 of the wearable subsystem 14. In this embodiment, the alignment member 136 may include a center key opening 138 configured to receive the center raised key member 141 and a peripheral opening 139 configured to receive the peripheral raised member 143. The alignment members 136, 140 may be configured to facilitate correct attachment of the wearable subsystem 114 to the sensing accessory 112 to ensure electrical connection therebetween. In an embodiment, the wearable subsystem 114 may be attached to an ostomy pouch or user via an adhesive pad 102 as shown in FIGS. 18-21.

During use, the wearable subsystem 14, 114 may poll resistance measurements from conductive traces to collect resistance data, which may be processed through an algorithm for determining an ostomy effluent leakage event. The algorithm may consider resistance measurements and other factors, such as resistance measurements from neighboring conductive traces, a change in resistance from recent prior resistance measurements, historical data from prior uses, etc.

Upon a detection of an ostomy effluent leakage event, the wearable subsystem 14, 114 may alert a user via sound, vibration, light, etc. according the leakage event. An alert may be sent based on resistance measurements received from multiple sensors, patterns in measurements, user preference inputs, signals received from other components of the ostomy leakage detection system, such as a mobile application and/or charging dock.

The wearable subsystem 14, 114 may be configured to communicate data to a mobile application. The data may be raw sensor data as received from the sensing accessory 12, 112 or processed data processed by the wearable subsystem 14, 114, which may include a summarized data and/or a leakage event information. The wearable subsystem 14, 114 may also be configured to communicate system conditions, such as the connectivity of the sensing accessory 12, 112, a faulty sensor, a state of battery, etc. The wearable subsystem 14, 114 may be powered by a battery or recharged by the charging dock 16. The wearable subsystem 14, 114 may include conductive pads on a charge circuit portion of the circuit board, which may be configured to contact pins on the charging dock 16.

Charging Dock

A charging dock 16 according to an embodiment is shown in FIGS. 23A-D. The charging dock 16 may comprise a medical grade power supply unit and a housing including charging pins 52 for electronically connecting to the wearable subsystem 14, 114. The housing may also include additional components, for example, a speaker and LEDs for sending alerts and feedback to a user, and a wireless communication module for communicating with the wearable subsystem 14, 114 and a mobile application.

The charging dock 16 may be configured to recharge a rechargeable battery of the wearable subsystem 14, 114. When the wearable subsystem 14, 114 is placed in a recessed area 54 of the charging dock 16, an electrical connection may be formed between the charging pins 52 and conductive pads of the wearable subsystem 14, 114. A charging circuit of the wearable subsystem 14, 114 may be configured to ensure a safe recharge.

In an embodiment, the charging dock 16 may be configured to provide an additional means for alerting a user about leakage events. When the charging dock 16 is in wireless communication with the wearable subsystem 14, 114, the user may have an option to receive leak alerts from the charging dock 16. This option may be most advantageous at night when other means of alerting may not be as effective for users during sleep. For example, a vibration alert from the wearable subsystem 14, 114 may not be effective to rouse a sleeping user. The user may also power down or disable sounds from a mobile phone at night. As such, the user may opt to receive alerts from the charging dock 16. The wearable subsystem 14, 114 may be configured to determines a leakage event and send a signal to the charging dock 16 via Bluetooth communication. The charging dock 15 may be configured to send an audible alert through a speaker and/or a visual alert through LEDs when a leakage event signal is received. Certain aspects of the alert, such as volume and duration, may be configurable by the user.

Mobile Application

The mobile application may be configured to provide means for users to interact with the ostomy leakage detection system 10. For example, a user may set preferences for alerts and review historical data, such as analysis of leakage patterns and usage trends, by using the mobile application. The mobile application may also be configured to functions as a resource for connecting the user to support, such as training materials, experts at the manufacturer, and ostomy clinicians.

The mobile application may be configured to communicate with the wearable subsystem 14, 114 and the charging dock 16 over Bluetooth. The mobile application may be configured to confirm these connections and alerts if a subsystem is unavailable. The mobile application may be configured to alert the user about leakage events and/or system issues through alert functions of a mobile phone, such as sound and vibration.

The mobile application may be configured to relay data to a cloud server for storage and/or data analysis, for example prediction of leaks based on repeated wears, comparison to the leakage patterns of other users of the system, or other factors. A communication link between a cloud system and the mobile application may allow for additional features, such as product recommendations based on leakage patterns or other data, re-ordering of products in a convenient or automatic format, direct consultation with a clinician, storage of photographs of the stoma or peristomal skin for tracking alongside leakage patterns, etc.

Figure 25:
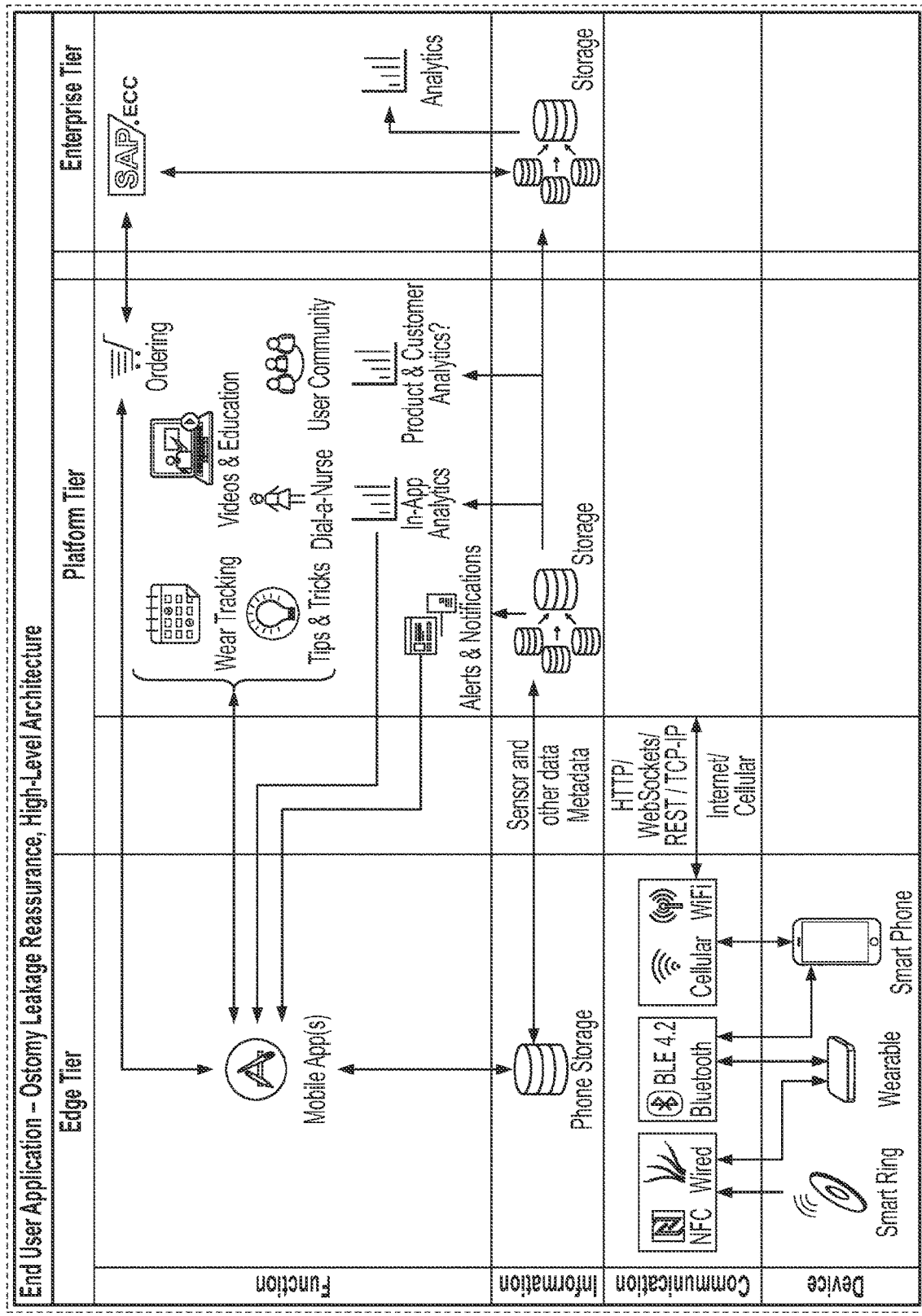
FIG. 25 is a diagram showing communication between subsystems of an ostomy leakage detection system according to an embodiment.

A diagram of communication between subsystems of the ostomy leakage detection system 10 and communication between the ostomy leakage detection system 10 and a cloud system according to an embodiment is shown in FIG. 25.

Method of Detecting Ostomy Effluent Leakage

The sensing accessory 12, 112 may be configured to detect an ostomy effluent leakage by measuring a change in resistance between electrodes, which are also referred to herein as conductive traces. When ostomy effluent bridges two electrodes, a resistance measurement between the electrodes may drop substantially to indicate a leakage event. In an embodiment, resistance below a predetermined threshold resistance value of 1 MΩ may identify a leakage event, which is selected to provide a necessary level of sensitivity to distinguish an ostomy effluent leakage event from other events causing a change in resistance, for example, user's perspiration.

Figure 24:
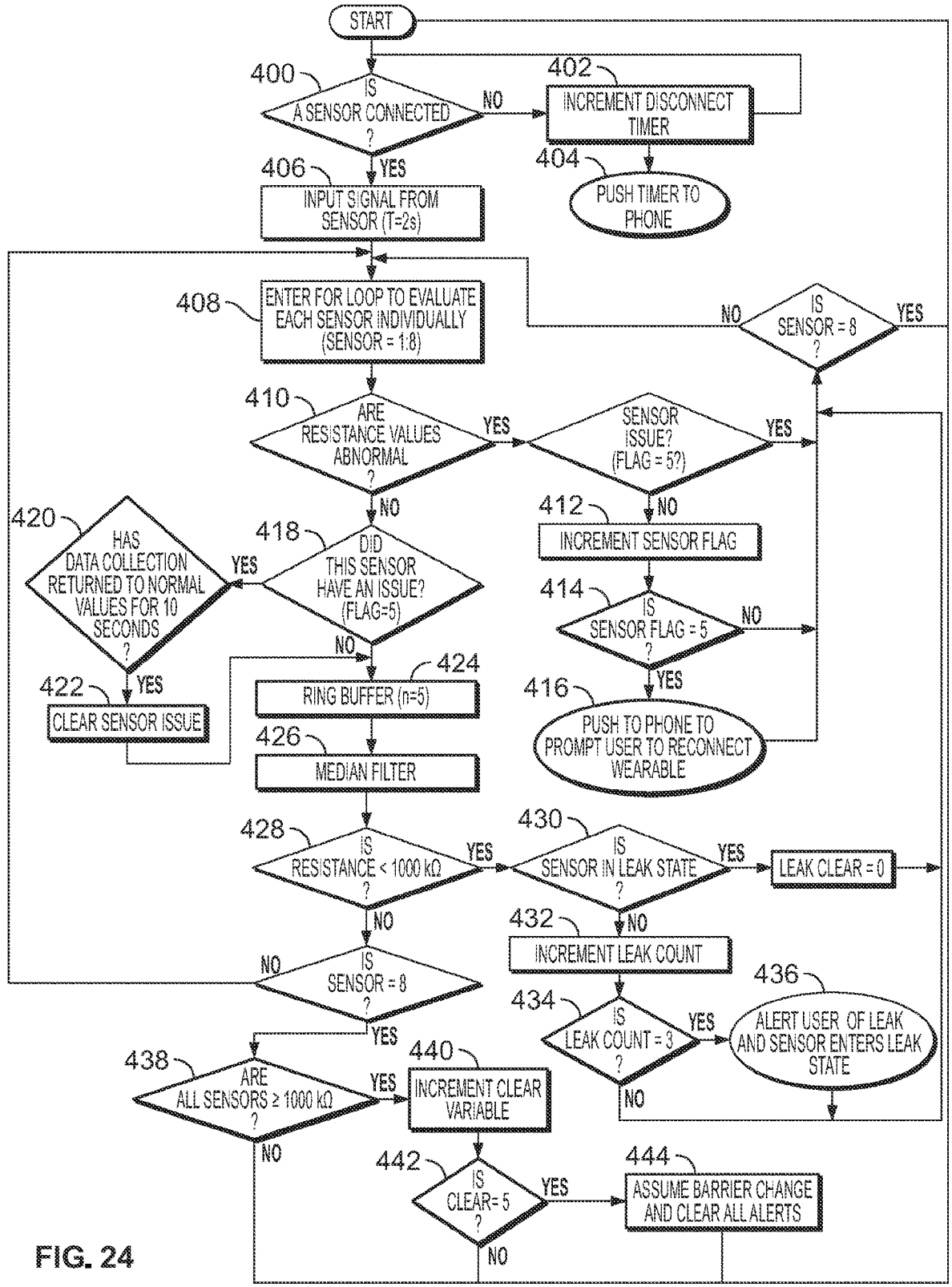

FIG. 24 is a block diagram for a method of detecting an ostomy effluent leakage using the ostomy leakage detection system 10 according to an embodiment. The steps of the method of detecting an ostomy effluent leakage may be configured for accurate determination of leakage events and to minimize false detections. The method may include the step of providing a sensing accessory 12, 112 comprising a plurality of sensors, for example, 8 sensors, arranged adjacent an adhesive or embedded in the adhesive. Each of the plurality of sensors may be formed from a pair of conductive traces configured to measure resistance of the adhesive.

The method may also include the step of determining whether the sensing accessory 12, 112 is electrically connected to the wearable subsystem 14, 114. In the step of "Is a sensor connected?" 400, the wearable subsystem 14, 114 may send a signal to the sensing accessory 12, 112 requesting a return signal. If no signal is returned, the wearable subsystem 14, 114 may determine that the sensing accessory 12, 112 is not connected and increase a disconnect timer in the step of "Increment disconnect timer" 402. The wearable subsystem 14, 114 may also send the disconnect timer data to an external device, such as user's phone, when the sensing accessory 12, 112 is not connected to the wearable device 14, 114 in the step of "Push time to phone" 404.

When the wearable device 14, 114 detects the sensing accessory 12, 112, the wearable device 14, 114 may pull a resistance measurement signal from each sensor in the step of "Input signal from sensor (T=2 s)" 406. In an embodiment, the wearable device 14, 114 may be configured to pull and receive a resistance measurement every 2 seconds. The signal received from each sensor may be processed separately in the step of "Enter for loop to evaluate each sensor individually (sensor=1:8)" 408. The signals may be processed by a processor provided in the wearable device 14, 114 to determine whether a resistance measured by a sensor is outside a predetermined range of acceptable resistance values in the step of "Are resistance values abnormal?" 410.

If the resistance measurement is outside the predetermined range of acceptable resistance values, for example, negative recorded resistance values, the sensor may be flagged in the step of "Increment sensor flag" 412. In the step of "Is sensor flag=5?" 414, the number of abnormal resistance measurements that fall outside the predetermined range of acceptable resistance values may be counted. If the number of abnormal resistance measurements reaches five, the wearable device 14, 114 may determine that an abnormal event has occurred and may send an alert to an external device, such as user's phone, in the step of "Push to phone to prompt user to reconnect wearable" 416. The alert may also instruct a user to take an action such as reconnecting the wearable subsystem 14, 114 to the sensing accessory 12, 112.

In an embodiment, an abnormal resistance value may not be entered in a ring buffer, which is configured to store resistance measurements, and a new resistance measurement from the same sensor or a resistance measurement from a different sensor may be taken. If an issue is detected at a sensor in the step of "Did this sensor have an issue? (Flag=5)" 418, but the resistance measurements for the same sensor returns to a normal value within the predetermined range of acceptable resistance values for 10 subsequent consecutive seconds, the issue may be cleared and the resistance measurement data may be entered in the ring buffer in the steps of "Has data collection returned to normal values for 10 seconds?" 420, "Clear sensor issue" 422, and "Ring buffer (n=5)" 424.

In an embodiment, the ring buffer may be configured to hold a current resistance measurement and four previous resistance measurements for each sensor, wherein the resistance measurements may be used to calculate a median filter value (a median of the five resistance measurements) in the step of "Median filter" 426. The ring buffer may be continuously pushed through the median filter which is a median of the last five resistance measurements. In an embodiment, the predetermined range of acceptable resistance values may be set at less than a threshold resistance value of 1 MΩ. In the step of "Is resistance<1000 kΩ?" 428, whether a median filter value of a sensor is less than the threshold value may be determined. If the median filter value of the sensor is less than the threshold value, the status of that sensor is checked in the step of "Is sensor in leak state?" 430. If the sensor is not already in a leak state, a leak count of the sensor may be incremented in the step of "Increment Leak Count" 432. In the step of "Is leak count=3?" 434, the number of median filter values that are less than the threshold value may be counted (i.e. leak count). If the leak count of the sensor reaches three, the sensor may be determined to be in a leak state and an alert including information regarding the leak state, such as the location of the sensor, may be pushed to an external device, such as user's phone in the step of "Alert user of leak and sensor enters leak state" 436.

If the median filter value of the sensor is determined to be greater than or equal to the threshold value (1 MΩ) in the step of "Is resistance<1000 kΩ?" 428, a resistance measurement from a next sensor is taken, and the steps of detecting an ostomy effluent leakage 408, 410, 412, 414, 416, 418, 420, 422, 424, 426, 428, 430, 432, 434, 436 may be repeated until resistance measurements from all of the sensors, for example eight sensors, are processed. If the median filter values of all of the sensors are determined to be greater than or equal to the threshold value or the maximum detectable resistance value, for example, 1541 kΩ, in the step of "Are all sensors≥1000 kΩ?" 438, the count of Clear for the sensors may be increased in the step of "Increment Clear variable" 440. If sensors are Clear for 5 consecutive times in the step of "Is Clear=5?", which may be 10 seconds in the embodiments wherein the resistance measurements are taken every 2 seconds, the sensors may be determined to be in a clear state and new resistance measurements are taken from the sensors for a next round of the leak detection analysis. If one or more sensors is determined to be in a leak state, leakage alerts may be cleared when a user changes the barrier in the step of "Assume barrier change and clear all alerts" 444.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A sensing accessory for detecting leakage in a medical device, comprising:
   a sensor region including a center opening and a plurality of sensors arranged around the center opening, wherein the plurality of sensors comprises at least two substantially elliptical conductive traces substantially surrounding the center opening and at least two arc-shaped conductive traces, wherein the at least two substantially elliptical conductive traces include a first trace and a second trace, and the at least two arc-shaped conductive traces comprises a first arc trace and a second arc trace, wherein each of the two substantially elliptical conductive traces is arranged at a different radial distance from the center opening, and each of the at least two arc-shaped conductive traces is arranged in a different sector in the sensor region;
   a connector region comprising a plurality of connection points at terminal ends of the plurality of sensors configured for electrical connection to an external device, and
   a tail region extending between the sensor region and connector region, the tail region having an elongated body.

2. The sensing accessory of claim 1, wherein the first trace is arranged at a first radial distance from the center opening, the second trace is arranged at a second radial distance from the center opening, the first arc trace is arranged at a third radial distance from the center opening, and the second arc trace is arranged at a fourth radial distance from the center opening, wherein the third and fourth radial distances are greater than the second radial distance and the second radial distance is greater than the first radial distance, such that the first trace, the second trace, and the first and second arc traces are arranged in substantially concentric layers substantially surrounding the center opening, wherein the sensing accessory is configured to measure a resistance of the medical device between the first trace and the second trace and between the second trace and each of the at least two arc-shaped conductive traces.

3. The sensing accessory of claim 1, wherein the first trace is a first level trace and the second trace is a first ground trace, and the at least two substantially elliptical conductive traces further include a second level trace, a fourth level trace, a fifth level trace, a second ground trace, and a third ground trace, and the at least two arc-shaped conductive traces further include a third arc trace and a fourth arc trace, wherein the first level trace is arranged at a first radial distance from the center opening, the first ground trace is arranged at a second radial distance from the center opening, a second level trace is arranged at a third radial distance from the center opening, the second ground trace is arranged at a fifth radial distance from the center opening, the third level trace is arranged at a sixth radial distance from the center opening, the fourth level trace is arranged at a seventh radial distance from the center opening, the third ground trace is arranged at an eighth radial distance from the center opening, and the first, second, third, and fourth arc traces are arranged at a fourth radial distance from the center opening, wherein the radial distances are first radial distance<second radial distance<third radial distance<fourth radial distance<fifth radial distance<sixth radial distance<seventh radial distance<eighth radial distance, such that the level traces, the ground traces, and the arc traces are arranged in eight substantially concentric layers substantially surrounding the center opening, wherein the sensing accessory is configured to measure a resistance of the medical device between the first level trace and the first ground trace, between the first ground trace and the second level trace, between each of the first, second, third, and fourth arc traces and the second ground trace, between the second ground trace and the fourth level trace, and between the fifth level trace and the third ground trace, wherein each of the first, second, third, and fourth arc traces is arranged in a different quadrant in the sensor region.

4. The sensing accessory of claim 3, wherein the first, second, third, and fourth arc traces are arranged in intercardinal directions of the sensor region with the tail region arranged at south, wherein the first arc trace extends along a southeast (SE) quadrant of the sensor region, wherein the second arc trace is formed from an exposed portion of a curved conductive trace extending along an east half of the sensor region with a lower portion covered with a masking layer to provide the second arc trace extending along a northeast (NE) quadrant of the sensor region, wherein the third arc trace is formed from an exposed portion of a curved conductive trace extending along an west half of the sensor region with a lower portion covered with a masking layer to provide the third arc trace extending along a northwest (NW) quadrant of the sensor region, and wherein the fourth arc trace extends along a southwest (SW) quadrant of the sensor region.

5. The sensing accessory of claim 4, wherein the sensing accessory is configured to measure a resistance of the medical device between the first level trace and the first ground trace for determination of a level 1 leakage, a resistance between the first ground trace and the second level trace for determination of a level 2 leakage, a resistance between the first arc trace and the second ground trace for determination of a level 3 leakage in the SE quadrant, a resistance between the second arc trace and the second ground trace for determination of a level 3 leakage in the NE quadrant, a resistance between the third arc trace and the second ground trace for determination of a level 3 leakage in the NW quadrant, a resistance between the fourth arc trace and the second ground trace for determination of a level 3 leakage in the SW quadrant, a resistance between the second ground trace and fourth level trace for determination of a level 4 leakage, and a resistance between the fifth level trace and the third ground trace for determination of a level 5 leakage, wherein a severity of a leakage is level 1 leakage<level 2 leakage<level 3 leakage<level 4 leakage<level 5 leakage, wherein the level 5 leakage is a critical leakage.

6. The sensing accessory of claim 1, wherein the at least two substantially elliptical conductive traces further include a third trace and a fourth trace, and the at least two arc-shaped conductive traces further include a third arc trace and a fourth arc trace, wherein the first trace is arranged at a first radial distance from the center opening, the second trace is arranged at a second radial distance from the center opening, a third trace is arranged at a fourth radial distance from the center opening, the fourth trace is arranged at a fifth radial distance from the center opening, and the first, second, third, and fourth arc traces are arranged at a third radial distance from the center opening, wherein the radial distances are first radial distance<second radial distance<third radial distance<fourth radial distance<fifth radial distance, such that the first, second, third, and fourth traces, and the first, second, third, and fourth arc traces are arranged in five substantially concentric layers substantially surrounding the center opening, wherein the first, second, third, and fourth arc traces are arranged in intercardinal directions of the sensor region with the tail region arranged at south, wherein the first arc trace extends along a southeast (SE) quadrant of the sensor region, wherein the second arc trace is formed from an exposed portion of a curved conductive trace extending along an east half of the sensor region with a lower portion covered with a masking layer to provide the second arc trace extending along a northeast (NE) quadrant of the sensor region, wherein the third arc trace is formed from an exposed portion of a curved conductive trace extending along an west half of the sensor region with a lower portion covered with a masking layer to provide the third arc trace extending along a northwest (NW) quadrant of the sensor region, and wherein the fourth arc trace extends along a southwest (SW) quadrant of the sensor region.

7. The sensing accessory of claim 6, wherein the sensing accessory is configured to measure a resistance of the medical device between the first trace and the second trace for determination of a level 1 leakage, a resistance between the second trace and the first arc trace for determination of a level 2 leakage in the SE quadrant, a resistance between the second trace and the second arc trace for determination of a level 2 leakage in the NE quadrant, a resistance between the second trace and the third arc trace for determination of a level 2 leakage in the NW quadrant, a resistance between the second trace and the fourth arc trace for determination of a level 2 leakage in the SW quadrant, a resistance between the first arc trace and the third trace for determination of a level 3 leakage in the SE quadrant, a resistance between the second arc trace and the third trace for determination of a level 3 leakage in the NE quadrant, a resistance between the third arc trace and the third trace for determination of a level 3 leakage in the NW quadrant, a resistance between the fourth arc trace and the third trace for determination of a level 3 leakage in the SW quadrant, and a resistance between the third trace and fourth trace to determine a level 4 leakage, wherein a severity of a leakage is level 1 leakage<level 2 leakage<level 3 leakage<level 4 leakage, wherein the level 4 leakage is a critical leakage.

8. The sensing accessory of claim 1, wherein the medical device is an ostomy appliance including a first adhesive layer configured to attach to a peristomal skin of a user, wherein the sensor region has a ring-like shape, and the center opening is configured to receive a stoma, wherein each of the at least two substantially elliptical conductive traces and the at least two arc-shaped conductive traces extends from the sensor region through the tail region to the connector region and terminates at the plurality of connection points, wherein the sensing accessory comprises a sensor layer having a body-side and a distal side, a second adhesive layer arranged on the body-side of the sensor layer, and a backing layer arranged on the distal side of the sensor layer, wherein the sensor layer includes a substrate and the plurality of sensors are provided on a body-side of the substrate and in contact with the second adhesive layer, wherein the sensing accessory is configured to measure a resistance of the second adhesive layer using the plurality of sensors, wherein exposed portions of the tail region of the sensor layer are covered with a tail cover, wherein the sensing accessory is configured to attach to the ostomy appliance, wherein the backing layer is configured to attach to the ostomy appliance, and the second adhesive layer is configured to attach to a peristomal skin of a user, wherein the second adhesive layer is a hydrocolloid adhesive.

9. The sensing accessory of claim 8, wherein the backing layer is formed from an adhesive, wherein the sensing accessory further comprises a body-side release liner covering the second adhesive layer and a distal side release liner covering the backing layer, wherein each of the release liners include a tab configured to facilitate removal of the release liners, and wherein the tabs are arranged offset from each other, wherein the release liners include indicator labels to guide assembling of the sensing accessory with the ostomy appliance and attachment of the assembled sensing accessory and ostomy appliance to a user.

10. The sensing accessory of claim 8, wherein the tail cover also covers a portion of the connector region and includes a wing-like extensions in the connector region, wherein an adhesive is provided on the wing-like extensions for attachment to an ostomy pouch or a user.

11. The sensing accessory of claim 8, wherein the second adhesive layer is configured to exhibit a resistance drop from greater than 2 M$\Omega$ to about 1 k$\Omega$ when the second adhesive layer is exposed to an ostomy effluent.

12. The sensing accessory of claim 8, wherein the sensing accessory is configured to be stretched to conform to a convex ostomy barrier, wherein the substrate and the plurality of sensors are formed from stretchable materials.

13. A leakage detection system for an ostomy appliance comprising:
the sensing accessory according to claim 1; and
a wearable subsystem configured to communicate with the sensing accessory and receive signals from the sensing accessory to detect an ostomy effluent leakage, wherein the wearable subsystem includes a hinged case comprising a bottom housing, a top housing, and a hinge connecting the bottom housing and the top housing, wherein the hinged case is configured to be closed after the wearable subsystem is connected to the connector region to secure the wearable subsystem to the sensing accessory, wherein the wearable subsystem is configured to analyze signals received from the sensing accessory, communicate with external devices, and alert a user to notify a leakage event and/or a status of the ostomy appliance,
wherein the tail region is flexible to allow the wearable subsystem to be attached to a user or to the ostomy appliance at various locations when the wearable subsystem is attached to the sensor accessory.

14. The leakage detection system of claim 13, wherein the connector region includes a first alignment member, and the wearable subsystem includes a second alignment member, wherein the first alignment member and the second alignment member are configured to engage with each other to facilitate correct alignment and connection between the sensing accessory and the wearable subsystem, wherein the first alignment member includes at least one opening in the connector region, and the second alignment member includes at least one raised member, wherein the at least one raised member is configured to be received in the at least one opening.

15. The leakage detection system of claim 14, wherein the second alignment member includes a center raised key member and a peripheral raised member, wherein the center raised key member is provided generally in a center of the bottom housing and the peripheral raised member is arranged proximate the hinge, wherein the first alignment member includes a center key opening configured to receive the center raised key member and a peripheral opening configured to receive the peripheral raised member, wherein the wearable subsystem further includes a plurality of conductive members configured to contact the plurality of connection points to electrically connect the wearable subsystem to the sensing accessory, wherein the plurality of conductive members are arranged proximate and surrounding the center raised key member, wherein the plurality of conductive members comprises a plurality of raised conductive pads.

16. The leakage detection system of claim 14, wherein the second alignment member includes first and second raised members, and the first alignment member includes a first opening configured to receive the first raised member and a second opening configured to receive the second raised member, wherein the wearable subsystem further includes a plurality of conductive members configured to contact the plurality of connection points to electrically connect the wearable subsystem to the sensing accessory, wherein the plurality of conductive members are arranged between the first and second raised member, wherein the plurality of conductive members comprises a plurality of raised conductive pads.

17. The leakage detection system of claim 13, wherein the wearable subsystem is configured to poll resistance measurements from the plurality of sensors to collect resistance data and process the resistance data through an algorithm to determine an ostomy effluent leakage event, and alert a user according a severity of the leakage event, and wherein the wearable subsystem is configured to detect and communicate a connectivity status between the wearable subsystem and the sensing accessory and a faulty sensor to a user or to an external device.

18. The leakage detection system of claim 13, wherein the wearable subsystem includes a rechargeable battery, and wherein the leakage detection system further includes a charging dock configured to charge the rechargeable battery of the wearable subsystem and to wirelessly communicate with the wearable subsystem to receive leakage signals and send an alert to a user, wherein the charging dock comprises a housing configured to receive the wearable subsystem and charging pins, wherein the wearable subsystem includes conductive pads configured to electrically connect to the charging pins, wherein the charging dock comprises a device to generate a sound and/or light to alert a user and a wireless communication module for communicating with the wearable subsystem and/or a mobile application.

19. The leakage detection system of claim 13, further comprising a mobile application configured to wirelessly communicate with the wearable subsystem and/or a charging dock, wherein the mobile application is provided as an application for a mobile phone, wherein the wearable subsystem is configured to transmit a data to the mobile application, wherein the data comprises resistance measurements as received from the sensing accessory and/or a processed data generated by processing the resistance measurements at the wearable subsystem, wherein the processed data includes a leakage event information and/or a summary of the resistance measurements, wherein the mobile application is configured to provide means for a user to interact with the leakage detection system to set user's preferences for alerts and to review information about the ostomy appliance, wherein the information includes data related to leakage patterns, historical data of user's ostomy appliance usage, and/or ostomy appliance usage trends, wherein the mobile application is configured to connect a user to ostomy training materials, experts at ostomy appliance suppliers, and/or ostomy clinicians, wherein the mobile application is configured to check a connectivity between the mobile application and the wearable subsystem and/or the charging dock and alert a user, wherein the mobile application is configured to receive a leakage event information from the wearable subsystem and alert a user through alert functions of a mobile phone.

20. The leakage detection system of claim 19, wherein the mobile application is configured to transmit data to a cloud server for storage and data analysis, wherein the data analysis is configured to provide a prediction of a leakage event based on user's historical data, a comparison data against leakage patterns of other users, product recommendations based on user's leakage patterns, and/or a prompt for re-ordering ostomy products, and wherein the mobile application is configured to manage a storage of photographs of user's stoma and/or peristomal skin for tracking with user's leakage patterns.

* * * * *